(12) United States Patent
Nishimura et al.

(10) Patent No.: US 9,618,772 B2
(45) Date of Patent: Apr. 11, 2017

(54) SPECTACLE LENS DESIGN SYSTEM, SUPPLY SYSTEM, DESIGN METHOD AND MANUFACTURING METHOD

(71) Applicant: HOYA CORPORATION, Tokyo (JP)

(72) Inventors: Hidetoshi Nishimura, Tokyo (JP); Tomohiro Odaira, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/771,425

(22) PCT Filed: Feb. 28, 2014

(86) PCT No.: PCT/JP2014/055176
§ 371 (c)(1),
(2) Date: Aug. 28, 2015

(87) PCT Pub. No.: WO2014/133166
PCT Pub. Date: Sep. 4, 2014

(65) Prior Publication Data
US 2016/0011437 A1    Jan. 14, 2016

(30) Foreign Application Priority Data

Feb. 28, 2013  (JP) ................................ 2013-039000
Mar. 5, 2013  (JP) ................................ 2013-042509

(51) Int. Cl.
*A61B 3/10*    (2006.01)
*A61B 3/00*    (2006.01)
(Continued)

(52) U.S. Cl.
CPC ............ *G02C 7/027* (2013.01); *A61B 3/0091* (2013.01); *A61B 3/111* (2013.01); *A61B 3/113* (2013.01);
(Continued)

(58) Field of Classification Search
USPC .................................................. 351/200–246
See application file for complete search history.

(56) References Cited

U.S. PATENT DOCUMENTS 5,576,778 A    11/1996  Fujie et al.
6,637,880 B1*  10/2003  Yamakaji ............... G02C 7/027
                                                351/159.75
(Continued)

FOREIGN PATENT DOCUMENTS

CN          1112700 A     11/1995
CN        101057170 A     10/2007
(Continued)

OTHER PUBLICATIONS

Funes Mora, Kenneth Alberto et al., "Gaze Estimation From Multimodal Kinect Data", pp. 4321-4326, (2012).
(Continued)

*Primary Examiner* — Mohammed Hasan
(74) *Attorney, Agent, or Firm* — Oliff PLC

(57) ABSTRACT

A spectacle lens design system, including: an eyeball rotation center determination means that identifies an corneal apex position of an eye of a subject based on an image photographed by a predetermined photographing apparatus and determines an eyeball rotation center position of the subject based on the identified corneal apex position; a visual line information calculation means that calculates visual line information of the subjected defined when the subject watches a visual target disposed at a predetermined position, based on the eyeball rotation center position determined by the eyeball rotation center determination means and the position of the visual target; and a shape design means that designs a shape of a spectacle lens based on
(Continued)

US 9,618,772 B2

Page 2 predetermined prescription information and the visual line information calculated by the visual line information calculation means.

17 Claims, 31 Drawing Sheets

(51) Int. Cl.
    *G02C 7/02*           (2006.01)
    *A61B 3/11*           (2006.01)
    *G02C 13/00*         (2006.01)
    *G02C 7/06*           (2006.01)
    *A61B 3/113*         (2006.01)

(52) U.S. Cl.
    CPC ............ *G02C 7/061* (2013.01); *G02C 13/005* (2013.01); *G02C 7/025* (2013.01)

(56) References Cited

U.S. PATENT DOCUMENTS

| | | | |
|---|---|---|---|
| 6,811,260 B2 | 11/2004 | Yamakaji | |
| 6,871,955 B2 | 3/2005 | Yamakaji et al. | |
| 6,979,084 B2 | 12/2005 | Qui | |
| 7,108,373 B2 | 9/2006 | Yamakaji | |
| 7,441,895 B2 | 10/2008 | Akiyama et al. | |
| 7,768,516 B1 | 8/2010 | Bourdev et al. | |
| 8,297,752 B2* | 10/2012 | Wada | G02C 7/027 351/200 |
| 8,360,580 B2* | 1/2013 | Chauveau | A61B 3/111 351/204 |
| 2003/0076479 A1 | 4/2003 | Qi | |
| 2003/0107702 A1 | 6/2003 | Yamakaji | |
| 2003/0123026 A1 | 7/2003 | Abitbol et al. | |
| 2004/0032565 A1 | 2/2004 | Yamakaji et al. | |
| 2005/0041205 A1 | 2/2005 | Yamakaji | |
| 2005/0088616 A1 | 4/2005 | Nason et al. | |
| 2007/0118428 A1 | 5/2007 | Akiyama et al. | |
| 2007/0279590 A1 | 12/2007 | Ebisawa | |
| 2010/0128220 A1 | 5/2010 | Chauveau | |
| 2010/0195045 A1 | 8/2010 | Nauche et al. | |
| 2012/0294478 A1 | 11/2012 | Publicover et al. | |

FOREIGN PATENT DOCUMENTS

| | | |
|---|---|---|
| EP | 1728467 A1 | 12/2006 |
| EP | 2369403 A1 | 9/2011 |
| JP | H10-66678 A | 3/1998 |
| JP | 3919097 B | 2/2007 |
| JP | 3919097 B2 | 5/2007 |
| JP | 4033344 B | 11/2007 |
| JP | 4033344 B2 | 1/2008 |
| JP | 2010-524011 A | 7/2010 |
| JP | 2010-243827 A | 10/2010 |
| JP | 2010-259605 A | 11/2010 |
| JP | 2010/266892 A | 11/2010 |
| JP | 2011-039551 A | 2/2011 |
| JP | 4649319 B2 | 3/2011 |
| JP | 4942661 B2 | 5/2012 |
| JP | 5279153 B1 | 9/2013 |
| JP | 2013-226397 A | 11/2013 |
| WO | 2006/054985 A1 | 5/2006 |

OTHER PUBLICATIONS

Viola, Paul et al., "Robust Real-Time Face Detection", International Journal of Computer Vision 57(2), pp. 137-154, (2004).
Fanelli, Gabriele et al., "Real Time Head Pose Estimation With Random Regression Forests", pp. 617-624, (2011).
Kim, Tae Kyun et al., "Real-Time Normalization and Feature Extraction of 3D Face Data Using Curvature Characteristics", Human Computer Interaction Lab, pp. 1-6.
Apr. 22, 2014 International Search Report issued in International Patent Application No. PCT/JP2014/055176.
Apr. 22, 2014 International Search Report issued in International Patent Application No. PCT/JP2014/055177.
U.S. Appl. No. 14/771,348, filed Aug. 28, 2015 in the name of Nishimura et al.
Sep. 11, 2015 International Preliminary Report on Patentability (Chapter I) issued in International Patent Application No. PCT/JP2014/055176.
Sep. 11, 2015 International Preliminary Report on Patentability (Chapter I) issued in International Patent Application No. PCT/JP2014/055177.
May 23, 2016 Office Action Issued in Chinese Patent Application No. 201480011364.8.
May 31, 2016 Office Action Issued in Chinese Patent Application No. 201480011349.3.
Aug. 11, 2016 Office Action Issued in U.S. Appl. No. 14/771,348.
Aug. 23, 2016 Office Action issued in Japanese Patent Application No. 2015-503066.
Nov. 21, 2016 Search Report issued in European Patent Application No. 14757565.8.
Nov. 23, 2016 Search Report issued in European Patent Application No. 14757686.2.

* cited by examiner

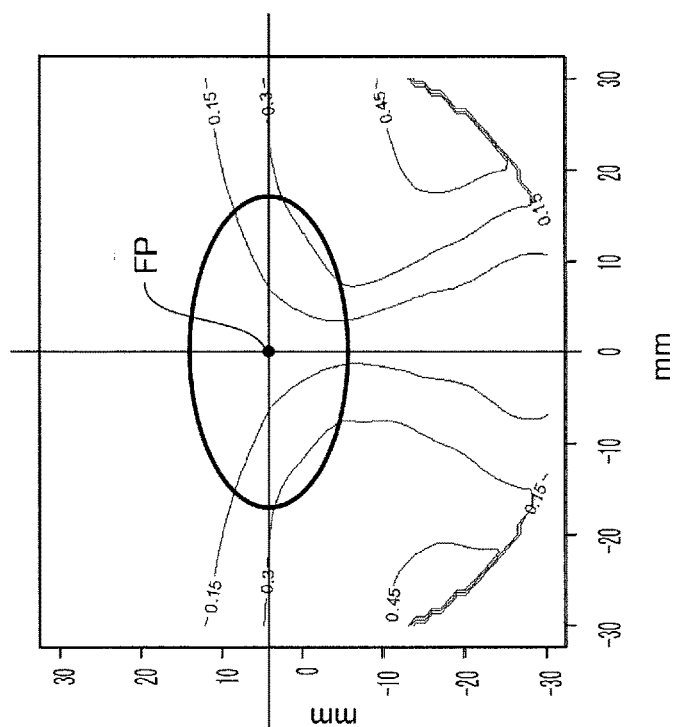
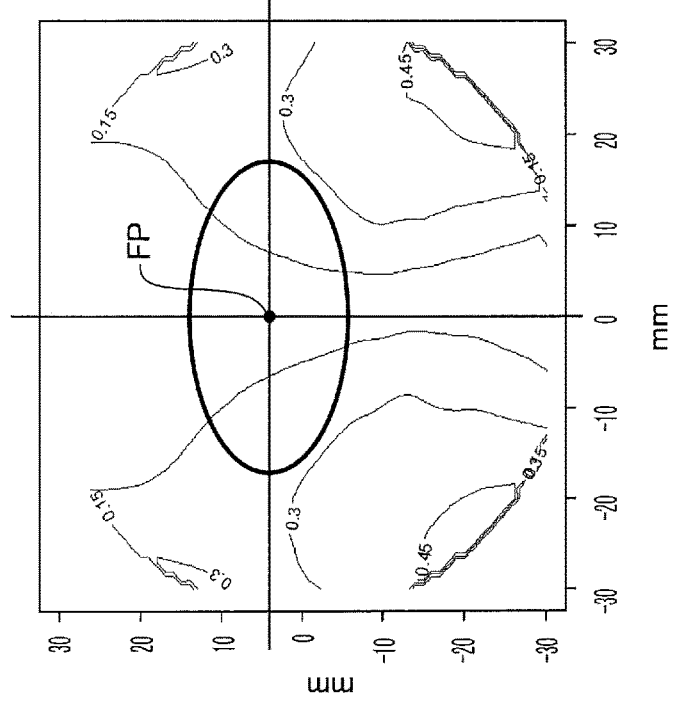
FIG. 26B
FIG. 26A

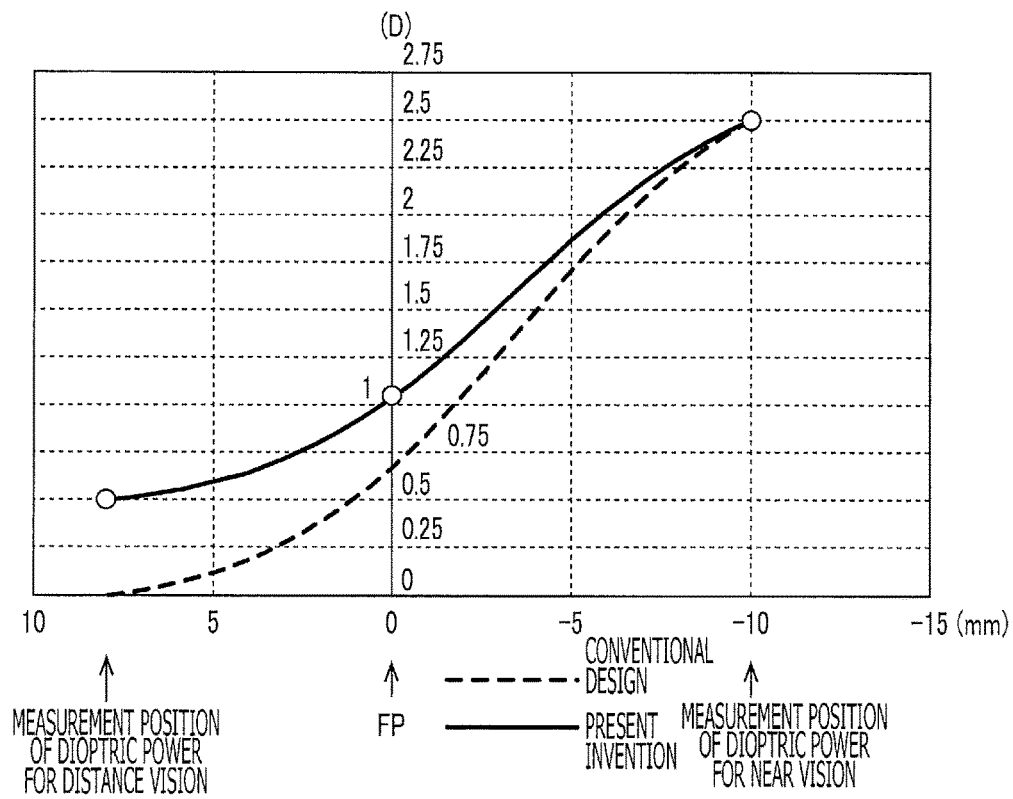
FIG. 35
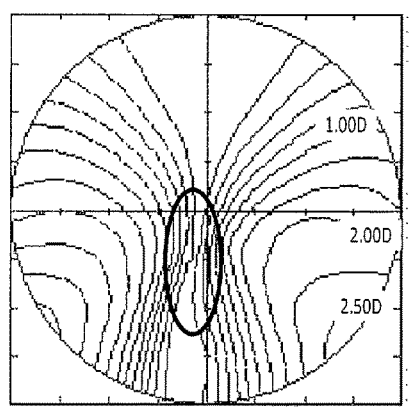
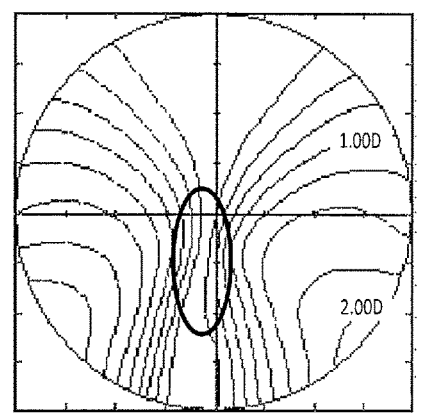
FIG. 36A   FIG. 36B

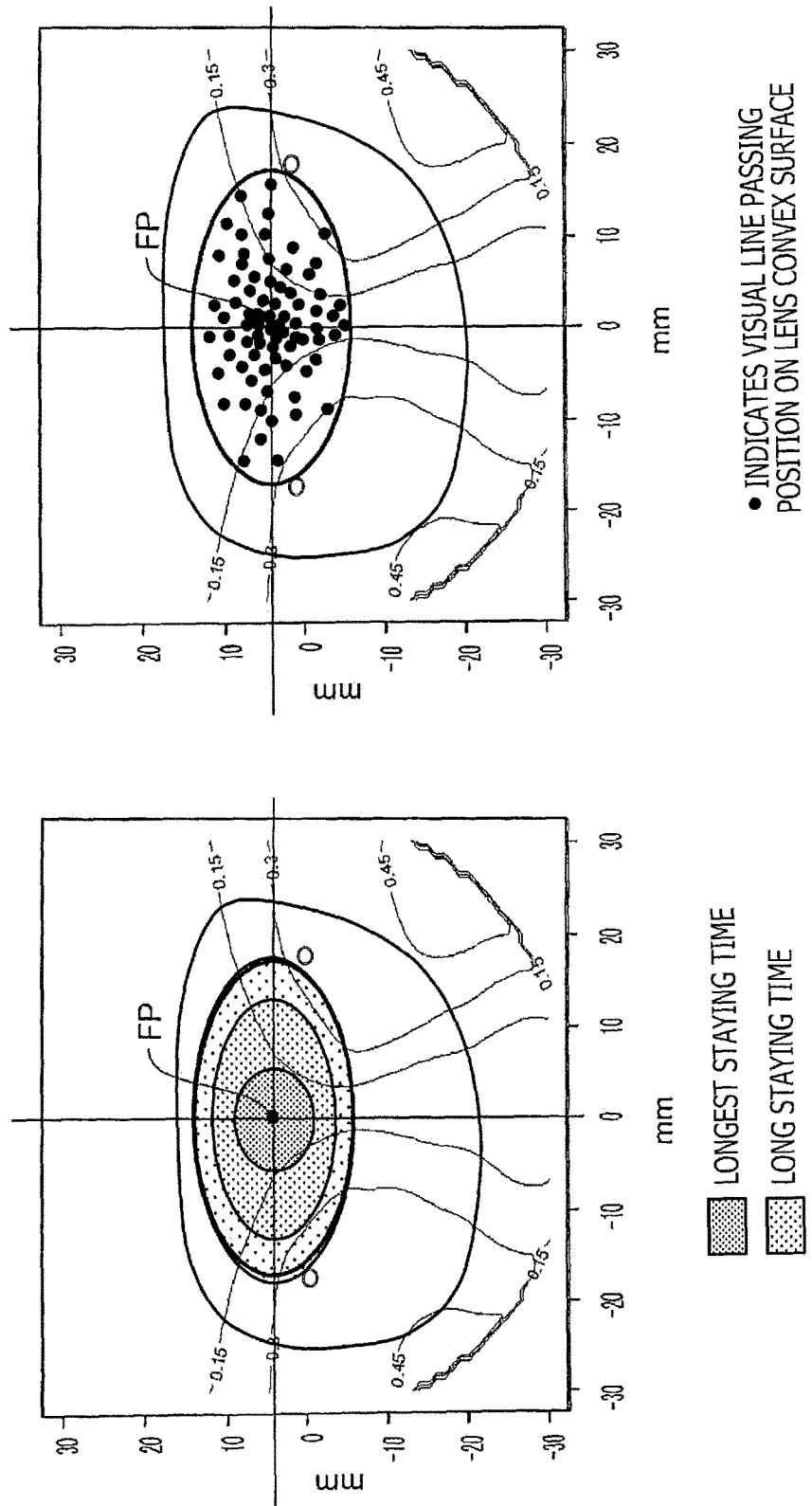

SPECTACLE LENS DESIGN SYSTEM, SUPPLY SYSTEM, DESIGN METHOD AND MANUFACTURING METHOD

TECHNICAL FIELD

The present invention relates a method for designing and manufacturing spectacle lenses using visual line information of a subject.

BACKGROUND ART

Recently, introducing visual line information of a scheduled wearer into design of spectacle lenses has been proposed in order to provide spectacle lenses more suitable for a customer (a scheduled wearer or a subject). A specific design method for such spectacle lenses is described, for example, in Japanese Patent Publication No. 4942661B (hereafter, referred to as patent document 1).

However, the design method described in patent document 1 is based on the premise that a scheduled wearer is supposed to wear spectacle lenses when measurement of visual lines is performed. Therefore, a problem that the design method is not able to support a scheduled wearer of naked eyes is pointed out.

SUMMARY OF THE INVENTION

Non-patent document 1 (Kenneth Alberto Funes Mora and Jean-Marc Odobez: "Gaze Estimation from Multimodal Kinetic Data" p. 4321-4326) describes technology where a subject and a visual target are photographed using an RGB-D camera capable of obtaining an RGB image and a distance image (depth information) and visual lines of the subject viewing the visual target are measured based on the photographed images. According to the method described in the non-patent document 1, the subject is in a naked eye condition when the measurement of the visual lines is performed.

For this reason, the inventor of the present invention has come up with an idea that, by introducing the measurement technology for visual lines described in the non-patent document 1 into design of spectacle lenses, it becomes possible to provide spectacle lenses having the aberration distribution suitable for movement of the visual lines regardless of whether or not a scheduled wearer is in a naked eye condition, and the inventor has made intensive studies. As a result, the inventor has found that it is impossible to simply introduce the measurement technology for visual lines described in the non-patent document 1 into design of spectacle lenses. Specifically, when spectacle lenses are designed using visual line information measured by the measurement technology for visual lines described in the non-patent document 1, if simulation in which a scheduled wearer performs near vision (e.g., reading) in a state of wearing spectacle lenses is executed, blur, shaking or distortion occurs. Therefore, it is found that aberration distribution suitable for visual lines for near vision is not achieved.

The present invention is made considering the above described circumstances. That is, the object of the present invention is to provide a design system, a supply system, a design method and a manufacturing method for spectacle lenses having aberration distribution suitable for each visual line distance.

A spectacle lens design system according to an embodiment of the invention comprises: an eyeball rotation center determination means that identifies an corneal apex position of an eye of a subject based on an image photographed by a predetermined photographing apparatus and determines an eyeball rotation center position of the subject based on the identified corneal apex position; a visual line information calculation means that calculates visual line information of the subjected defined when the subject watches a visual target disposed at a predetermined position, based on the eyeball rotation center position determined by the eyeball rotation center determination means and the position of the visual target; and a shape design means that designs a shape of a spectacle lens based on predetermined prescription information and the visual line information calculated by the visual line information calculation means.

It is considered that one of factors which cause, particularly during near vision, blur, shake, distortion and the like on the spectacle lens designed using visual line information measured by visual line measurement technology described in non-patent document 1 is the fact that a start point (a corneal apex) of the visual line information is different from an origin (the eyeball rotation center) defined in design of the spectacle lens. For this reason, in the embodiment of the invention, the visual line information is calculated while setting the start point of the visual line information at the eyeball rotation center which is equal to the origin defined in the design of the spectacle lens. By designing the spectacle lens using such visual line information, it is possible to prevent occurrence of an error of a direction and a distance of a visual line caused by the difference between the start point of the visual line information and the origin defined in design of the spectacle lens. That is, according to the embodiment of the invention, by using the above described visual line information, the spectacle lens having the aberration distribution suitable for each visual line information can be designed.

The spectacle lens design system may further comprise a wearing parameter calculation means that calculates a wearing parameter based on the corneal apex position identified based on the image photographed by the predetermined photographing apparatus. In this case, the shape design means designs the shape of the spectacle lens using the wearing parameter calculated by the wearing parameter calculation means.

The wearing parameter may include at least one of a frame pantoscopic angle, a frame face form angle, a frame vertex distance, a pupillary distance and a near working distance.

The wearing parameter calculation means may continuously calculate the wearing parameter as time series data, and determines a true wearing parameter by using values calculated continuously as the time series data.

When a coordinate system whose origin is equal to a reference point set at the predetermined photographing apparatus is defined as a photographing apparatus coordinate system, and a coordinate system whose origin is equal to a reference point set at a head of the subject is defined as a head coordinate system, the eyeball rotation center determination means may operate to: calculate a position and a pose of the head of the subject in the photographing apparatus coordinate system based on the image photographed by the predetermined photographing apparatus; define the head coordinate system based on the calculated position and the pose of the head of the subject; convert a coordinate of the corneal apex position in the photographing apparatus coordinate system to the corneal apex position in the head coordinate system by making directions of coordinate axes of the defined head coordinate system and directions of coordinate axes of the defined photographing apparatus coordinate system coincide with each other by performing predetermined coordinate conversion; and obtain a coordinate of a position of the eyeball rotation center by adding a default value to the coordinate of the corneal apex position in the converted head coordinate system.

The spectacle lens design system may further comprise: a detection means that detects, at predetermined time intervals, the position and the pose of the head based on the image photographed by the predetermined photographing apparatus or detected data by a detecting apparatus capable of detecting the position and the pose of the head of the subject; and a pseudo moving means that moves, at predetermined time intervals, the position of the visual target, in a pseudo manner, by an amount corresponding to a difference of the position of the head before and after detection by the detection means and a difference of the pose of the head before and after detection by the detection means so that the position and the pose of the head of the subject is maintained, in a pseudo manner, before and after the detection. In this case, the visual line information calculation means may calculate the visual line information based on the determined eyeball rotation center position and the position of the visual target moved in a pseudo manner.

The image may be photographed by the predetermined photographing apparatus at a predetermined frame rate, and in the eyeball rotation center determination means, tentative positions of the eyeball rotation center may be calculated for a predetermined number of frame images by determining eyeball rotation center positions for a predetermined number of frames, and a true eyeball rotation center position may be determined based on the calculated tentative positions in the predetermined number of frame images.

The visual line information may be vector information of a visual line including a vector length and a unit vector of a visual line connecting the eyeball rotation center position with the position of the visual target.

The visual line information further may include time axis information of the visual line. The spectacle lens design system may further comprise: a tentative shape design means that designs a tentative shape of the spectacle lens based on predetermined prescription information; a use calculation means that calculates a position on a spectacle lens through which a visual line defined when the subject wears a spectacle lens having the tentative shape passes, and a staying time of the visual line at the calculated position on the spectacle lens, based on the vector length, the unit vector and the time axis information of the visual line included in the visual line information calculated by the visual line information calculation means, and thereby calculates a use region and a use frequency in the spectacle lens by the subject; and a correction means that corrects the tentative shape based on the calculated use region and the use frequency.

The spectacle lens design system may further comprise a visual line information displaying means that displays information concerning the calculated visual line information.

A spectacle lens supply system according to an embodiment of the invention comprises: one of the above described spectacle lens design systems; and a spectacle lens manufacturing apparatus that manufactures spectacle lenses using design data by the spectacle lens design system.

A spectacle lens design method according to an embodiment of the invention, comprises: a photographing step of photographing a subject with a predetermined photographing apparatus; a determination step of identifying an corneal apex position of an eye of the subject based on an image photographed by the photographing step and determining an eyeball rotation center position of the subject based on the identified corneal apex position; a calculation step of calculating visual line information of the subjected defined when the subject watches a visual target disposed at a predetermined position, based on the eyeball rotation center position determined by the determination step and the position of the visual target; and a shape design step of designing a shape of a spectacle lens based on predetermined prescription information and the visual line information calculated by the calculation step.

In the embodiment of the invention, the visual line information is calculated while setting the start point of the visual line information at the eyeball rotation center which is equal to the origin defined in the design of the spectacle lens. By designing the spectacle lens using such visual line information, it is possible to prevent occurrence of an error of a direction and a distance of a visual line caused by the difference between the start point of the visual line information and the origin defined in design of the spectacle lens. That is, according to the embodiment of the invention, by using the above described visual line information, the spectacle lens having the aberration distribution suitable for each visual line information can be designed.

The spectacle lens design method may further comprise a wearing parameter calculation step of calculating a wearing parameter based on the corneal apex position identified based on the image photographed by the predetermined photographing apparatus. In this case, in the shape design step, the shape of the spectacle lens may be designed using the calculated wearing parameter.

The wearing parameter may include at least one of a frame pantoscopic angle, a frame face form angle, a frame vertex distance, a pupillary distance and a near working distance.

In the wearing parameter calculation step, the wearing parameter is continuously calculated as time series data, and a true wearing parameter is determined by using values calculated continuously as the time series data.

In the spectacle lens design method, when a coordinate system whose origin is equal to a reference point set at the predetermined photographing apparatus is defined as a photographing apparatus coordinate system, and a coordinate system whose origin is equal to a reference point set at a head of the subject is defined as a head coordinate system, in the determining step a position and a pose of the head of the subject in the photographing apparatus coordinate system may be calculated based on the image photographed by the predetermined photographing apparatus; the head coordinate system may be defined based on the calculated position and the pose of the head of the subject; a coordinate of the corneal apex position in the photographing apparatus coordinate system may be converted to the corneal apex position in the head coordinate system by making directions of coordinate axes of the defined head coordinate system and directions of coordinate axes of the defined photographing apparatus coordinate system coincide with each other by predetermined coordinate conversion; and a coordinate of a position of the eyeball rotation center may be obtained by adding a default value to the coordinate of the corneal apex position in the converted head coordinate system.

The design method may perform a detection step of repeatedly detecting the position and the pose of the head based on the image photographed by the predetermined photographing apparatus or detected data by a detecting apparatus capable of detecting the position and the pose of the head of the subject; and a pseudo moving step of repeatedly moving, in a pseudo manner, the position of the visual target by an amount corresponding to a difference of the position of the head before and after detection by the detection means and a difference of the pose of the head before and after detection. In this case, in the calculation step the visual line information may be calculated based on the eyeball rotation center position determined in the determination step and the position of the visual target moved in a pseudo manner by the pseudo moving step.

In the photographing step, the image may be photographed at a predetermined frame rate. In this case, tentative positions of the eyeball rotation center may be calculated for a predetermined number of frame images by executing the determination step for a predetermined number of frames, and a true eyeball rotation center position may be determined based on the calculated tentative positions in the predetermined number of frame images.

The visual line information is, for example, vector information of a visual line including a vector length and a unit vector of a visual line connecting the eyeball rotation center position with the position of the visual target.

The visual line information further may include time axis information of the visual line.

The spectacle lens design method according to an embodiment of the invention further comprise: a tentative shape design step of designing a tentative shape of the spectacle lens based on predetermined prescription information; a use calculation step of calculating a position on a spectacle lens through which a visual line defined when the subject wears a spectacle lens having the tentative shape passes, and a staying time of the visual line at the calculated position on the spectacle lens, based on the vector length, the unit vector and the time axis information of the visual line included in the visual line information calculated by the calculation step, and thereby calculating a use region and a use frequency in the spectacle lens by the subject; and a correction step of correcting the tentative shape based on the calculated use region and the use frequency.

The spectacle lens design method may further comprise a visual line information displaying step of displaying information concerning the calculated visual line information.

A spectacle lens manufacturing method according to an embodiment of the invention comprises a spectacle lens manufacturing process of manufacturing the spectacle lens designed by the above described method.

BRIEF DESCRIPTION OF THE DRAWINGS

FIG. 26 shows distribution of logMAR visual acuity before and after optimization according to a design example 2.

FIG. 35 is a graph illustrating an addition power curve in a design example 4-2 and an addition power curve in conventional design.

FIG. 36 illustrates transmission astigmatism in the design example 4-2 and transmission astigmatism in conventional design.

FIG. 39 illustrates an example an image in which a design result, a frame and visual line information are arranged to overlap with each other.

EMBODIMENTS FOR CARRYING OUT THE INVENTION

In the following, a spectacle lens manufacturing system (a spectacle lens supply system) according to an embodiment of the invention is described with reference to the accompanying drawings.

Spectacle Lens Manufacturing System 1

Figure 1:
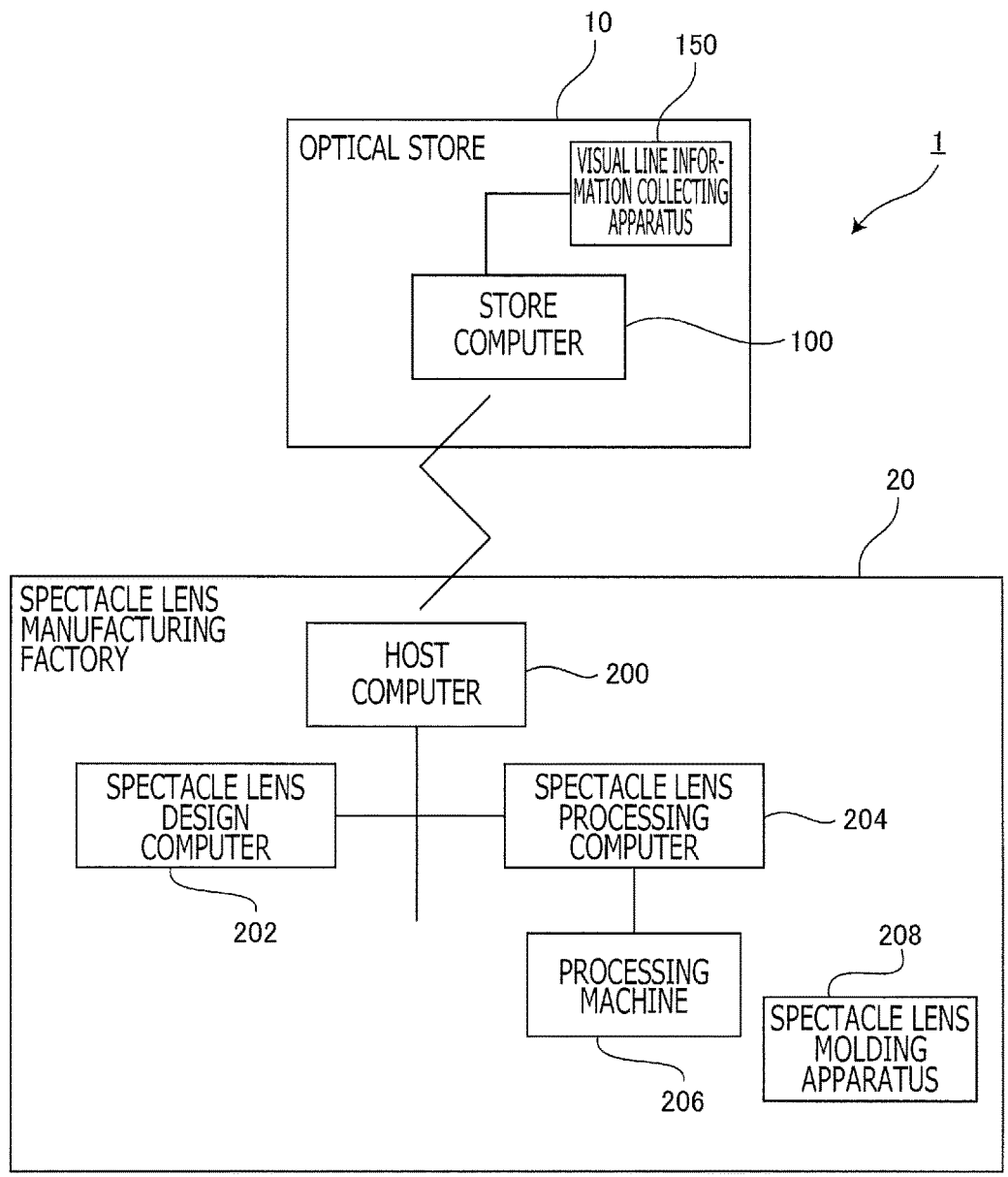
FIG. 1 is a block diagram illustrating a configuration of a spectacle lens manufacturing system according to an embodiment of the invention.

FIG. 1 is a block diagram illustrating a configuration of a spectacle lens manufacturing system 1 according to the embodiment. As shown in FIG. 1, the spectacle lens manufacturing system 1 includes an optical store 10 which orders spectacle lenses according to a prescription for a customer (a scheduled wearer or a subject), and a spectacle lens manufacturing factory 20 which manufactures spectacle lenses after receiving the order from the optical store 10. The order to the spectacle lens manufacturing factory 20 is issued through a predetermined network, such as the Internet, or data transmission by, for example, facsimile. Orderers may include ophthalmologists or general consumers.

Optical Store 10

In the optical store 10, a store computer 100 and a visual line information collecting apparatus 150 are installed. The store computer 100 is, for example, a general PC (Personal Computer), and software for ordering spectacle lenses to the spectacle lens manufacturing factory 20 has been installed in the store computer 100. To the store computer 100, lens data and frame data are input through an operation to a mouse or a keyboard by an optical store staff. Further, to the store computer 100, the visual line information collecting apparatus 150 is connected via a network, such as a LAN (Local Area Network), or a serial cable, and visual line information of a scheduled wearer collected by the visual line information collecting apparatus 150 is input to the store computer 100. The lens data includes, for example, visual line information collected by the visual line information collecting apparatus 150, a prescription (e.g., spherical power, cylindrical power, a cylindrical axis direction, prismatic power, prism base setting, an addition power and PD (Pupillary Distance) and the like), lens material, a refractive index, the type of optical design, a lens outer diameter, a lens thickness, a peripheral part thickness, decentering, a base curve, a wearing condition of spectacle lenses (a corneal vertex distance, a lens pantoscopic angle, a lens face form angle), the type of spectacle lens (a single-vision spherical lens, a single-vision aspherical lens, a multifocal lens (a bifocal lens or a progressive power lens)), coating (dyeing processing, hard coating, anti-reflection coating, ultraviolet light cutting and the like), and layout data according to a customer's request. The frame data includes shape data of a frame selected by a customer. The frame data is managed, for example, by barcode tags, and can be obtained by reading a barcode tag adhered to a frame by a barcode reader. The store computer 100 transmits the ordering data (the lens data and the frame data) to the spectacle lens manufacturing factory 20 via, for example, the Internet.

Spectacle Lens Manufacturing Factory 20

In the spectacle lens manufacturing factory 20, a LAN (Local Area Network) centering at a host computer 200 to which various terminal devices including a spectacle lens design computer 202 and a spectacle lens processing computer 204 are connected is constructed. Each of the spectacle lens design computer 202 and the spectacle lens processing computer 204 is a general PC. On the spectacle lens design computer 202 and the spectacle lens processing computer 204, a program for spectacle lens design and a program for spectacle lens processing are installed, respectively. To the host computer 200, the ordering data transmitted via the Internet is input from the store computer 100. The host computer 200 transmits the ordering data input thereto to the spectacle lens design computer 202.

Manufacturing of Spectacle Lenses in Spectacle Lens Manufacturing Factory 20

Figure 2:
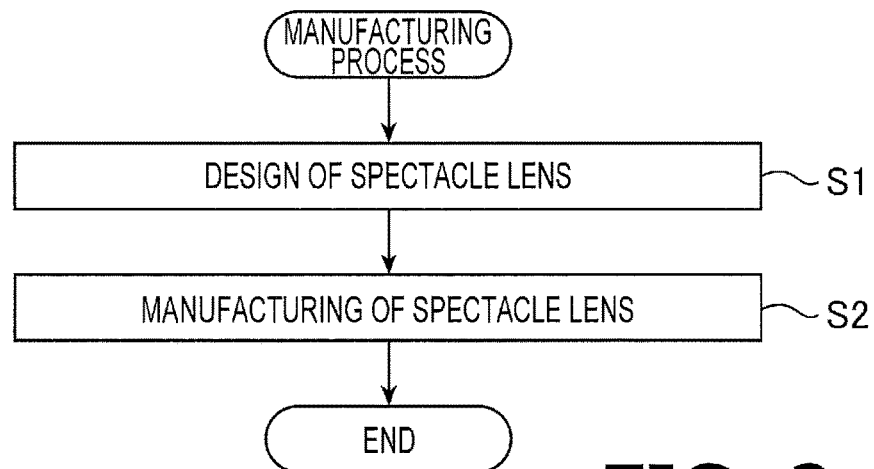
FIG. 2 is a flowchart illustrating a manufacturing process for spectacle lenses according to the embodiment of the invention.

S1 in FIG. 2 (Design of Spectacle Lens)

FIG. 2 is a flowchart illustrating a manufacturing process for spectacle lenses in the spectacle lens manufacturing factory 20. In the spectacle lens design computer 202, a program for designing spectacle lenses in response to received order has been installed, and the spectacle lens design computer 202 creates design data and edge processing data based on ordering data. Design of spectacle lenses using the spectacle lens design computer 202 is explained in detail later. The spectacle lens design computer 202 transfers the created lens design data and the edge processing data to the spectacle lens processing computer 204.

S2 in FIG. 2 (Manufacturing of Spectacle Lens)

The spectacle lens processing computer 204 reads the lens design data and the edge processing data transferred from the spectacle lens design computer 202, and drives and controls a processing machine 206.

Let us consider, for example, a case where a plastic spectacle lens is manufactured by a cast polymerization method. In this case, the processing machine 206 makes molding dies respectively corresponding to an outer surface (a convex surface) and an inner surface (a concave surface) of a lens by grinding and polishing material, such as metal, glass or ceramics, in accordance with the lens design data. The pair of molding dies thus made is disposed to face with each other at an interval corresponding to the thickness of the spectacle lens, and an adhesive tape is wound around an outer circumferential surface of the both molding dies so that the interval between the both molding dies is sealed. When the pair of molding dies is set on a spectacle lens molding apparatus 208, a hole is opened in a part of the adhesive tape, and lens material liquid is injected into a cavity (a sealed space between the both molding dies) through the hole. The lens material liquid injected and filled into the cavity is then polymerized and cured by heat or ultraviolet irradiation. As a result, a polymer (a lens base material) to which a peripheral shape defined by transfer surface shapes of the pair of molding dies and the adhesive tape has been transferred is obtained. The lens base material obtained by the cast polymerization method is then removed from the molding dies. The removed lens base material is then subjected to removal of residual stress by an annealing process, and various coatings, such as, dyeing processing, hard coating, anti-reflection coating and ultraviolet light cutting. Thus, spectacle lenses are completed and are delivered to the optical store 10.

In order to enhance productivity, in the spectacle lens manufacturing factory 20, the whole production range of dioptric powers is divided into a plurality of groups, and semi-finished lens blank groups having convex surface curve shapes (e.g., a spherical shape or an aspherical shape) and lens diameters complying with respective production ranges are prepared in advance in preparation for orders. The semi-finished lens blank is, for example, a resin blank or a glass blank of which convex and concave surfaces are an optical surface (a finished surface) and a non-optical surface (an unfinished surface), respectively. In this case, an optimum semi-finished lens blank is selected based on the lens data, and the selected semi-finished lens blank is set on the processing machine 206. The processing machine 206 grinds and polishes the concave surface of the semi-finished lens blank set on the processing machine 206, so as to make an uncut lens. The uncut lens of which concave surface shape has been made is then subjected to various coatings, such as, dyeing processing, hard coating, anti-reflection coating and ultraviolet light cutting. The outer circumferential surface of the uncut lens after being subjected to the various coatings is then subjected to the peripheral processing based on the edge processing data. The spectacle lenses processed into circular shapes are then delivered to the optical store 10.

Method for Collecting Visual Line Information by Visual Line Information Collecting Apparatus 150

As described above, it is found through studies made by the inventor of the present invention that, when spectacle lenses are designed using visual line information measured by the measurement technology for visual lines described in the non-patent document 1, if simulation in which a scheduled wearer performs near vision (e.g., reading) in a state of wearing spectacle lenses is executed, blur, shaking or distortion occurs, and therefore, it is found that aberration distribution suitable for visual lines for near vision is not achieved. It is appropriate to set a start point of a visual line at an eyeball rotation center because in general a spectacle lens is designed by defining the eyeball rotation center as an origin. On the other hand, in the technology for measuring a visual line described in the non-patent document 1, a corneal apex is set as a start point of a visual line. When a visual target (an end point of a visual line) is at a distant position (i.e., in the case of a distance vision), an effect on design of a spectacle lens caused by a shift of a direction and a distance of the visual line resulting from the difference of the start points is small. However, when a visual target (an end point of a visual line) is at a near position (i.e., in the case of a near vision), an effect of on design of a spectacle lens caused by a shift of a direction and a distance of the visual line resulting from the difference of start points is large. It is considered that one of factors of not being able to obtain aberration distribution suitable for the visual line for the near vision when the spectacle lens is designed while introducing the technology for measuring the visual line described in the non-patent document 1 is the fact that the corneal apex is set as the start point of the visual line. Therefore, in the following, three examples (example 1 to 3) regarding a visual line information collecting process for collecting visual line information of a scheduled wearer suitable for designing and manufacturing a spectacle lens having aberration distribution suitable for every visual line distance ranging from a near point to a distant point are explained.

Example 1

Configuration of Visual Line Information Collecting Apparatus 150

Figure 3:
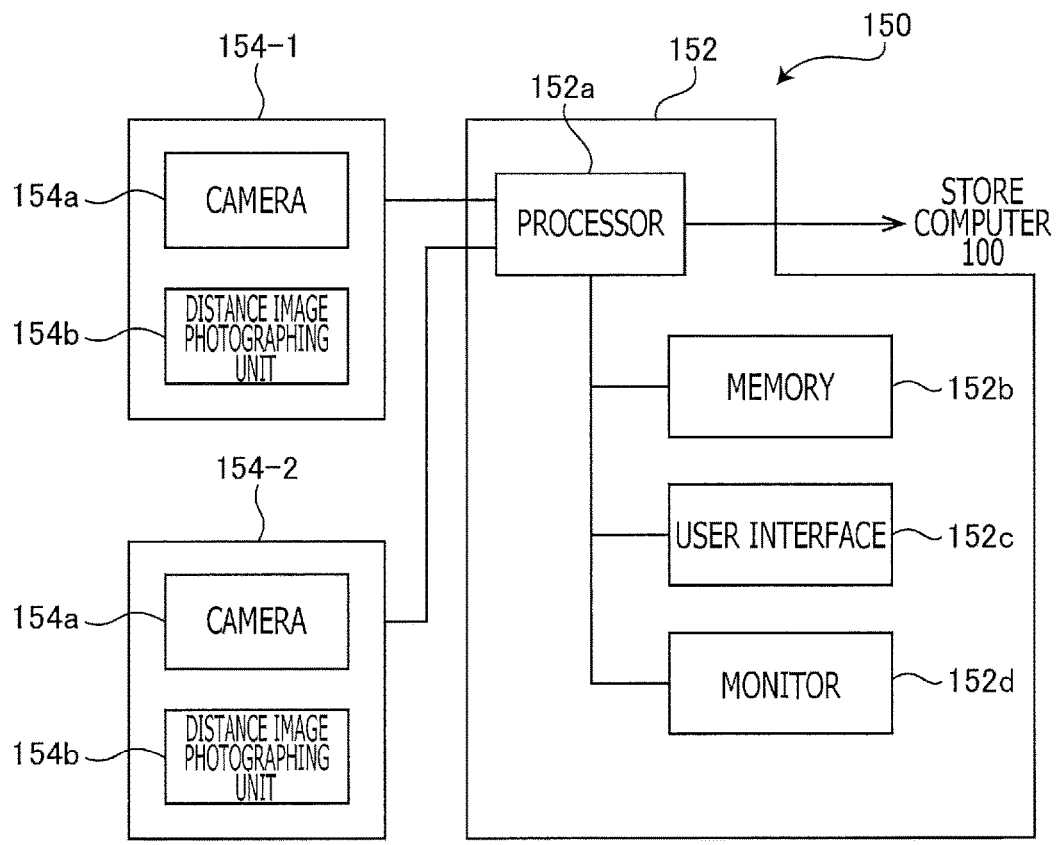
FIG. 3 is a block diagram illustrating a configuration of a visual line information collecting apparatus according to an example 1 of the invention.

FIG. 3 is a block diagram illustrating a configuration of the visual line information collecting apparatus 150 according to the example 1. As shown in FIG. 3, the visual line information collecting apparatus 150 according to the example 1 includes an information processing terminal 152, and RGB-D cameras 154-1 and 154-2.

The information processing terminal 152 is a terminal, such as a desktop PC (Personal Computer), a laptop PC, a notebook PC, a tablet PC, or a smart phone, and includes a processor 152a, a memory 152b, a user interface 152c and a monitor 152d. The processor 152a totally controls components in the visual line information collecting apparatus 150. The processor 152a operates to collect visual line information of a scheduled wearer by executing various programs stored in the memory 152b. The user interface 152c is an input device, such as a mouse and a keyboard. The optical store staff is able to operate the visual line information collecting apparatus 150 via the user interface 152c. For example, a GUI (Graphical User Interface) required for collecting the visual line information of a scheduled wearer by the visual line information collecting apparatus 150 is displayed on the monitor 152d.

Each of the RGB-D cameras 154-1 and 154-2 includes a camera 154a and a distance image photographing unit 154b. The camera 154a is a digital camera capable of photographing a two-dimensional RGB image of a subject. The distance image photographing unit 154b is a sensor capable of photographing a distance image. The distance image is a two dimensional image in which each of pixels constituting the image has information regarding a depth direction (i.e., distance information regarding the subject). Each of pixels constituting the distance image has correspondence with each of pixels constituting the RGB image by the camera 154a. It should be noted that the RGB-D camera itself is known, and can be seen, for example, in the non-patent document 1.

The processor 152a is able to generate a subject image having three dimensional information by calculating three dimensional coordinate data of each corresponding pixel in the RGB image by the camera 154a based on the depth information (the distance image) of each pixel constituting the distance image inputted from the distance image photographing unit 154b. In this example, by utilizing and improving the three dimensional image generating function, collection of the visual line information by the visual line information collecting apparatus 150 is made possible.

Figure 4:
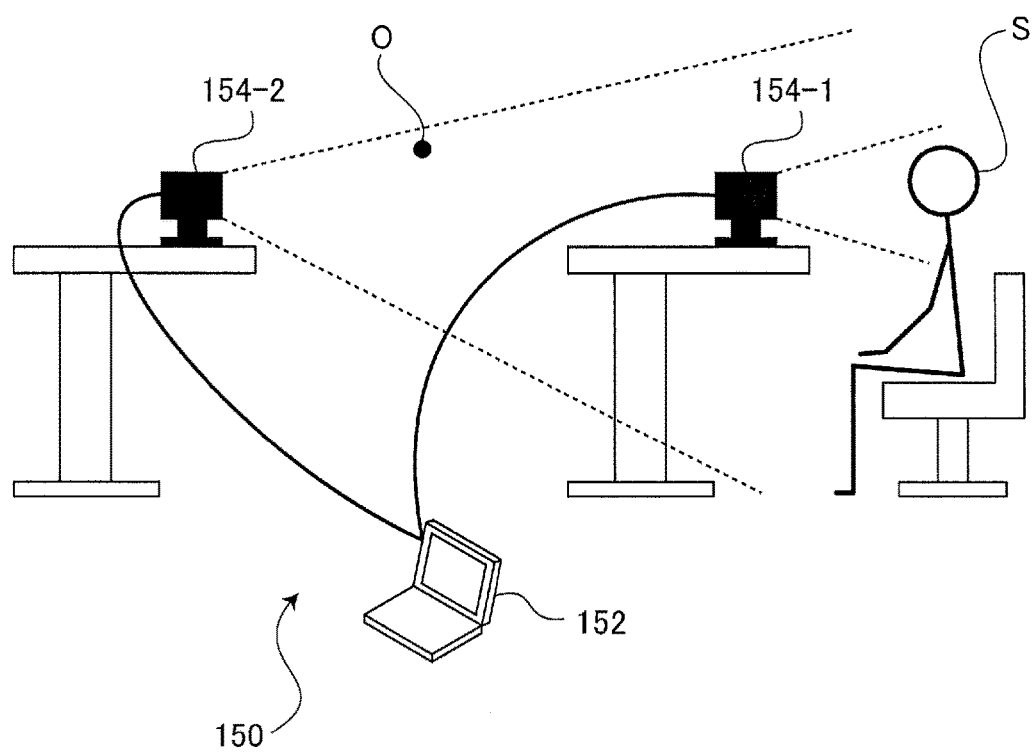
FIG. 4 illustrates a use condition of the visual line information collecting apparatus according to the example 1 of the invention.
Figure 5:
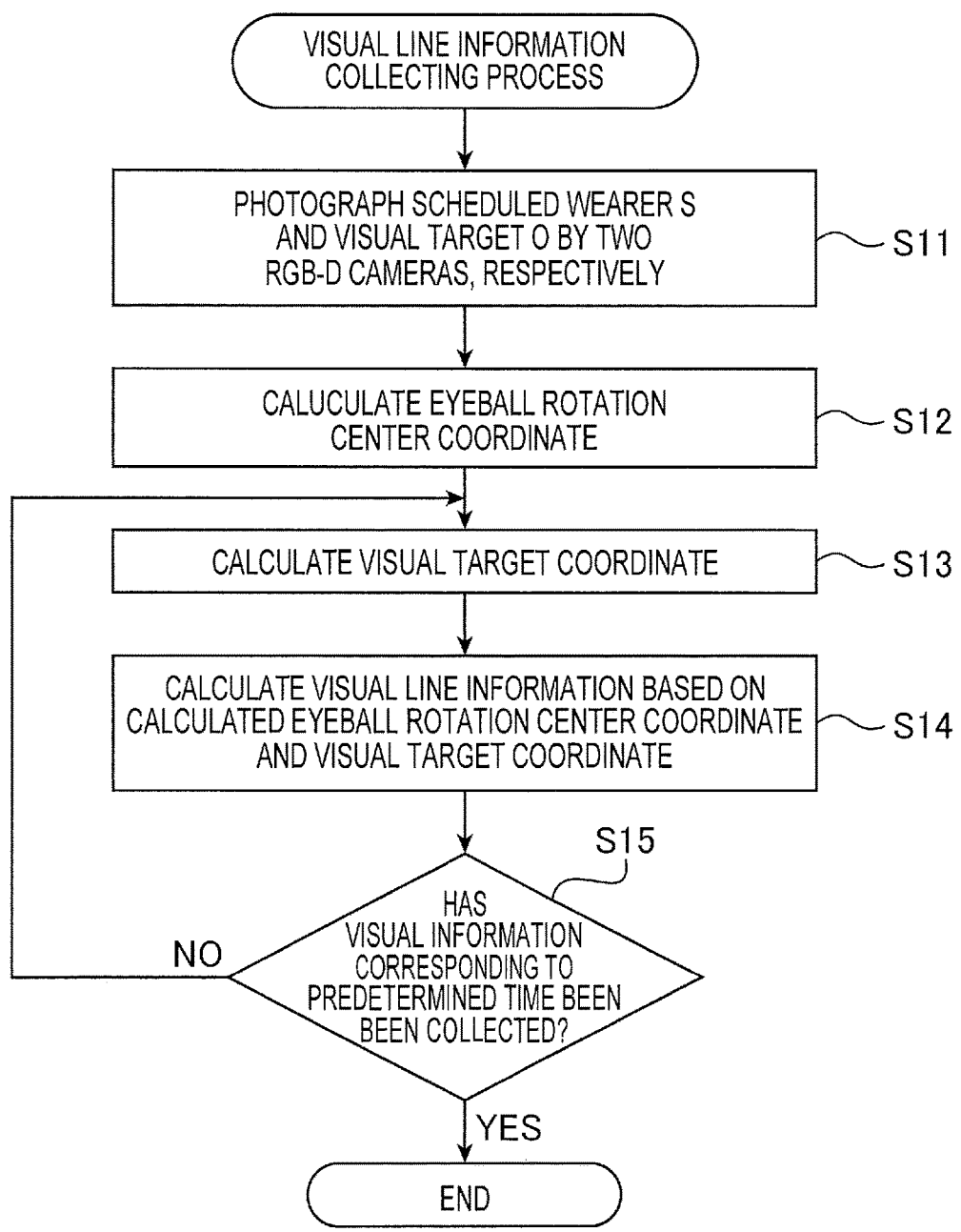
FIG. 5 is a flowchart illustrating a visual line information collecting process according to the example 1 of the invention.

FIG. 4 illustrates a use condition of the visual line information collecting apparatus 150 according to the example 1. FIG. 5 is a flowchart illustrating a visual line information collecting process by the visual line information collecting apparatus 150 used in the use condition shown in FIG. 4. As shown in FIG. 4, the RGB-D camera 154-1 is installed on a table. In the example shown in FIG. 4, a scheduled wearer S sits on a chair placed close to the RGB-D camera 154-1, and is instructed to watch the RGB-D camera 154-1 side. In addition, at a position further from the RGB-D camera 154-1 viewed from the scheduled wearer S and on the rear side of the RGB-D camera 154-1, a table is installed. On the table placed on the rear side of the RGB-D camera 154-1, the RGB-D camera 154-2 is installed. In order that the relative position between the scheduled wearer S and the RGB-D cameras 154-1 and 154-2 is made adjustable, the position, the height of a seating surface of the chair, and the position and the height of a top board of each table are made adjustable.

Visual Line Information Collecting Process by Visual Line Information Collecting Apparatus 150

S11 in FIG. 5 (Photographing Process by RGB-D Camera)

The RGB-D camera 154-1 photographs an RGB image and a distance image of the scheduled wearer S at a predetermined frame rate. The RGB-D camera 154-2 also photographs an RGB image and a distance image of a visual target O at a predetermined frame rate and at the timing synchronized with the RGB-D camera 154-1.

S12 in FIG. 5 (Calculation Process of Eyeball Rotation Center Coordinate)

The processor 152a calculates a coordinate $v_{rc1}$ of the eyeball rotation center which is a start point of a visual line of the scheduled wearer S. Broadly speaking, in step S12, a tentative value of the eyeball rotation center coordinate $v_{rc1}$ is calculated (steps S12a to S12g in FIG. 6 described later) for each of the frames photographed by the RGB-D camera 154-1 in step S11 (photographing process by RGB-D camera) in FIG. 5. When a sufficient number of tentative values for obtaining statistics are obtained, an average value of the tentative values is determined as a definitive value (the definitive value is defined as a true eyeball rotation center) of the eyeball rotation center coordinate $v_{rc1}$ (steps S12h and S12i in FIG. 6 described later). It is desirable that the scheduled wearer S pays attention to the followings for calculation of the eyeball rotation center coordinate $v_{rc1}$.

Face directly forward against the RGB-D camera 154-1 to photograph both eyes.

Do not move the head during the photographing.

Remove Spectacle lenses if the scheduled wearer wears the spectacle lenses in order to enhance the detection accuracy of the corneal apex of each eye.

Figure 6:
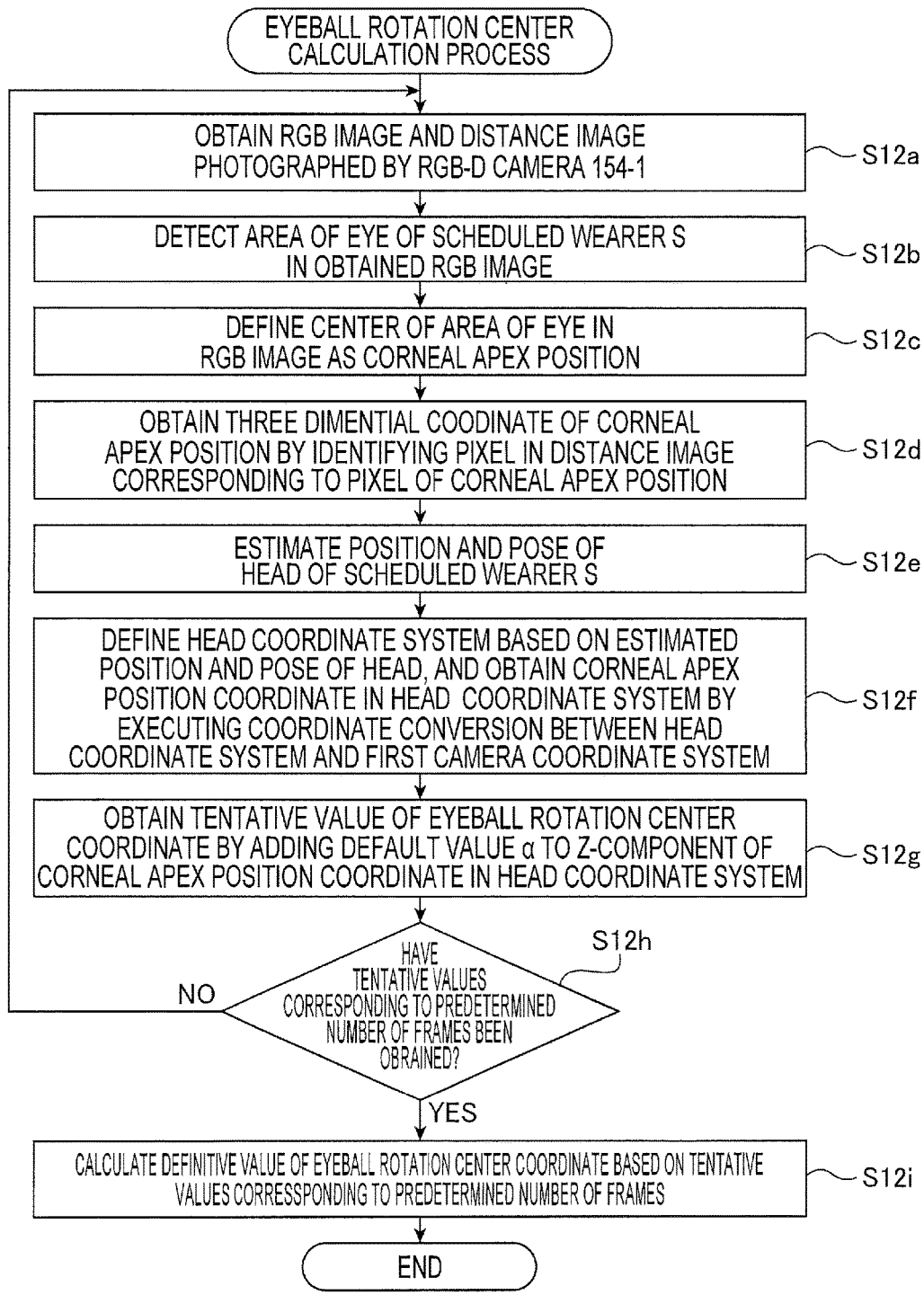
FIG. 6 is a flowchart illustrating step S12 (calculation process of eyeball rotation center coordinate) in FIG. 5.

FIG. 6 is a flowchart illustrating in detail step S12.

Step S12a in FIG. 6

The processor 152a obtains the RGB image and the distance image photographed by the RGB-D camera 154-1 in step S11 (photographing process by RGB-D camera) in FIG. 5.

Step S12b in FIG. 6

The processor 152a detects an area of an eye of the scheduled wearer S in the RGB image by analyzing the RGB image obtained by the RGB-D camera 154-1. For example, by using the know technique described in non-patent document 2 (Paul Viola and Michel J. Jones: "Robust Real-Time Face Detection", International Journal of Computer Vision 57(2), pp. 137-154, (2004)), the area of the eye of the scheduled wearer S can be detected.

Step S12c in FIG. 6

The processor 152a identifies a coordinate of the corneal apex in the RGB image by regarding the corneal apex as lying at the center of the area of the eye detected in step S12b in FIG. 6. That is, a pixel positioned at the center of the area of the eye detected in step S12b in FIG. 6 is regarded as a pixel on which the corneal apex is photographed.

Step S12d in FIG. 6

The processor 152a identifies a pixel in the distance image corresponding to the pixel (the coordinate of the corneal apex in the RGB mage) identified in step S12c in FIG. 6. As a result, the three dimensional coordinate $(x_c, y_c, z_c)$ of the corneal apex is obtained.

Step S12e in FIG. 6

Figure 7:
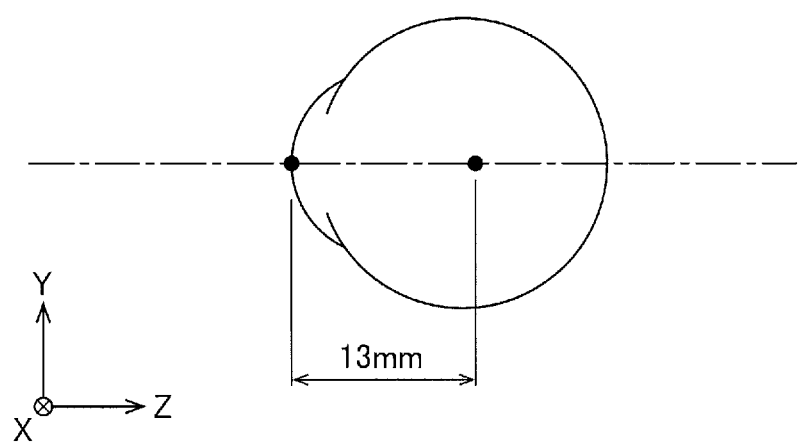
FIG. 7 illustrates an example of an eyeball model.

By using a known eyeball model, the three dimensional coordinate $v_{rc1}$ of the eyeball rotation center is calculated from the corneal apex coordinate $(x_c, y_c, z_c)$. Let us consider, for example, a case where a model eye of Gullstrand is used. In this case, the eyeball rotation center is regarded as being situated on the rear side by 13 mm along the Z-axis from the corneal apex (see an eyeball model in FIG. 7).

As described above, the scheduled wearer S is instructed to face directly forward against the RGB-D camera 154-1; however, the head of the scheduled wearer does not necessarily face directly forward the RGB-D camera 154-1 during the photographing. The wording "face forward directly" as used herein means a state in which the direction of the coordinate system (the coordinate axis) of the RGB-D camera 154-1 coincides with the direction of the coordinate system (the coordinate axis) of the head of the scheduled wearer S.

Figure 8A:
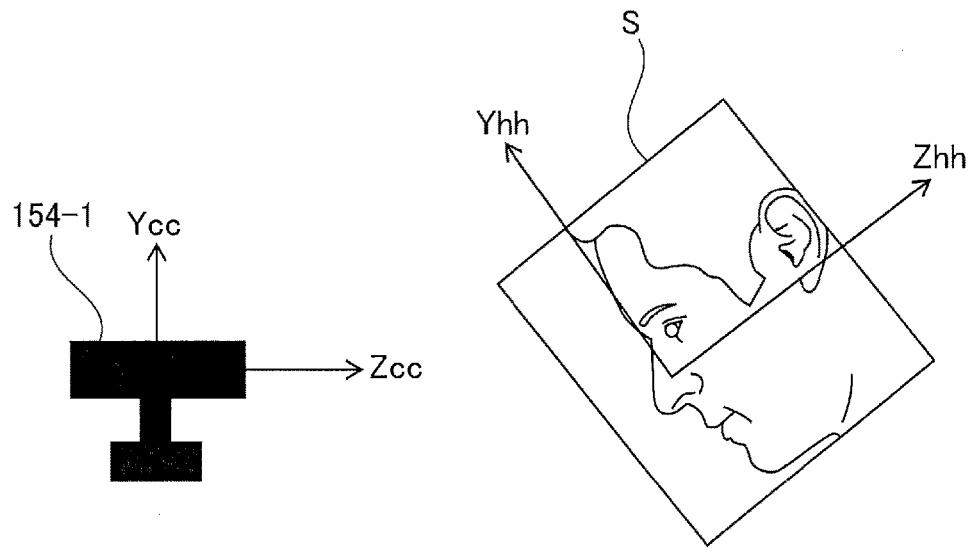
FIG. 8 illustrates a coordinate system of an RGB-D camera and a coordinate system of a head of a scheduled wearer according to the example 1 of the invention.
Figure 8B:
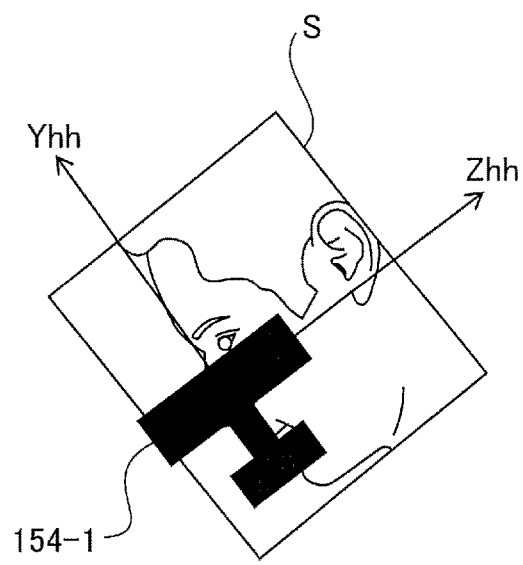

In each of FIGS. 8A and 8B, the coordinate system of the RGB-D camera 154-1 and the coordinate system of the head of the scheduled wearer S are shown. As shown in each of FIGS. 8A and 8B, the coordinate system of the RGB-D camera 154-1 is defined as a coordinate system having the origin equal to the optical center of the RGB-D camera 154-1, and hereafter the coordinate system is referred to as a "first camera coordinate system". The first camera coordinate system has the X axis extending in the horizontal direction of the RGB-D camera 154-1, the Y axis (assigned a symbol "Ycc" in FIG. 8 for convenience of explanation) extending in the vertical direction of the RGB-D camera 154-1, and the Z axis (a direction pointing to the frontward of the RGB-D camera 154-1 is a plus direction, and is assigned a symbol "Zcc" in FIG. 8 for convenience of explanation) extending in the depth direction of the RGB-D camera 154-1. The coordinate system of the head of the scheduled wearer S is a coordinate system having the origin defined at a predetermined point in the head (e.g., a center of a nose), and is hereafter referred to as a "head coordinate system". The head coordinate system has the X axis extending in the horizontal direction of the head of the scheduled wearer S, the Y axis (assigned a symbol "Yhh" in FIG. 8 for convenience of explanation) extending in the vertical direction of the head, and Z axis extending in the depth direction of the head (a direction pointing to the depth side is a plus direction and is assigned a symbol "Zhh" in FIG. 8 for convenience of explanation).

Let us consider a case where the direction of the first camera coordinate system does not coincide with the head coordinate system as shown in FIG. 8A. In this case, when the coordinate value equivalent to 13 mm is added to the Z component of the corneal apex coordinate $(x_c, y_c, z_c)$ in the first camera coordinate system, such addition of the coordinate value is divided into a Y component and a Z component in the head coordinate system. Therefore, it is understood that eyeball rotation center coordinate $v_{rc1}$ cannot be calculated precisely. In order to precisely calculate the eyeball rotation center coordinate $v_{rc1}$, at least it is necessary to let the direction of the first camera coordinate system coincide with the direction of the head coordinate system. For this reason, in step S12e, the processor 152a estimates the position and the pose of the head of the scheduled wearer S based on the distance image obtained by the RGB-D camera 154-1. For example, by using the know technique described in non-patent document 3 (Gabriele Fanelli, Juergen Gall, and Luc Van Gool: "Real Time Head Pose Estimation with Random Regression Forests" (2011)), it is possible to estimate the position and the pose of the head of the scheduled wearer S based on the distance image obtained by the RGB-D camera 154-1. The position is defined by three axes of XYZ, and the pose is defined by a roll angle, a yaw angle and a pitch angle.

Step S12f in FIG. 6

The processor 152a defines the head coordinate system based on the position and pose of the head of the scheduled wearer S estimated in step S12e in FIG. 6. By performing predetermined coordinate conversion, the processor 152a converts the corneal apex coordinate $(x_c, y_c, z_c)$ in the first camera coordinate system to the corneal apex coordinate $(x_h, y_h, z_h)$ in the head coordinate (see FIG. 8B). By executing step S12f, a state where the scheduled wearer S points directly forward against the RGB-D camera 154-1 is attained in regard to processing on software.

Step S12g in FIG. 6

By adding a default value a (a value corresponding to 13 mm in this embodiment) to the Z component of the corneal apex coordinate $(x_h, y_h, z_h)$ converted in step S12f in FIG. 6, the processor 152a obtains the eyeball rotation center coordinate $v_{rc1}$ $(x_h, y_h, z_h+\alpha)$. The eyeball rotation center coordinate $v_{rc1}$ $(x_h, y_h, z_h+\alpha)$ obtained here is an eyeball rotation center coordinate in a given frame, and is a tentative value. It should be noted that the default value $\alpha$ is not limited to the value corresponding to 13 mm. Strictly speaking, the distance between the corneal apex and the eyeball rotation center is not uniquely defined when considering various factors, such as, a race, gender, age and visual acuity. Therefore, the default value a more suitable for the scheduled wearer S may be settable by selecting an appropriate default value a (an eyeball model) considering these factors.

Step S12h in FIG. 6

Steps S12a to S12g of FIG. 6 are executed for each frame. In step S12h, the processor 152a judges whether the tentative values of the eyeball rotation center coordinates $v_{rc1}$ $(x_h, y_h, z_h+\alpha)$ corresponding to a predetermined number of frames have been obtained by executing the steps S12a to S12g of FIG. 6 for a plurality of times. When the processor 152a judges that the tentative values of the eyeball rotation center coordinates $v_{rc1}$ $(x_h, y_h, z_h+\alpha)$ corresponding to the predetermined number of frames have been obtained (S12h: YES), the process proceeds to step S12i in FIG. 6. When the processor 152a judges that the tentative values of the eyeball rotation center coordinates $v_{rc1}$ $(x_h, y_h, z_h+a)$ corresponding to the predetermined number of frames have not been obtained (S12h: NO), the process returns to step S12a in FIG. 6 and steps S12a to S12g of FIG. 6 are executed for a next frame.

Step S12i in FIG. 6

The predetermined number of frames is sufficient for obtaining statistics. Therefore, the processor 152a calculates the average value of the tentative values corresponding to the predetermined number of frames, and defines the calculated average value as the definitive value of the eyeball rotation center coordinates $v_{rc1}$ $(x_h, y_h, z_h+\alpha)$. Thus, the eyeball rotation center coordinates $v_{rc1}$ $(x_h, y_h, z_h+\alpha)$ being the start point of the visual line is obtained.

S13 in FIG. 5 (Calculation Process for Visual Target Coordinate)

Figure 9:
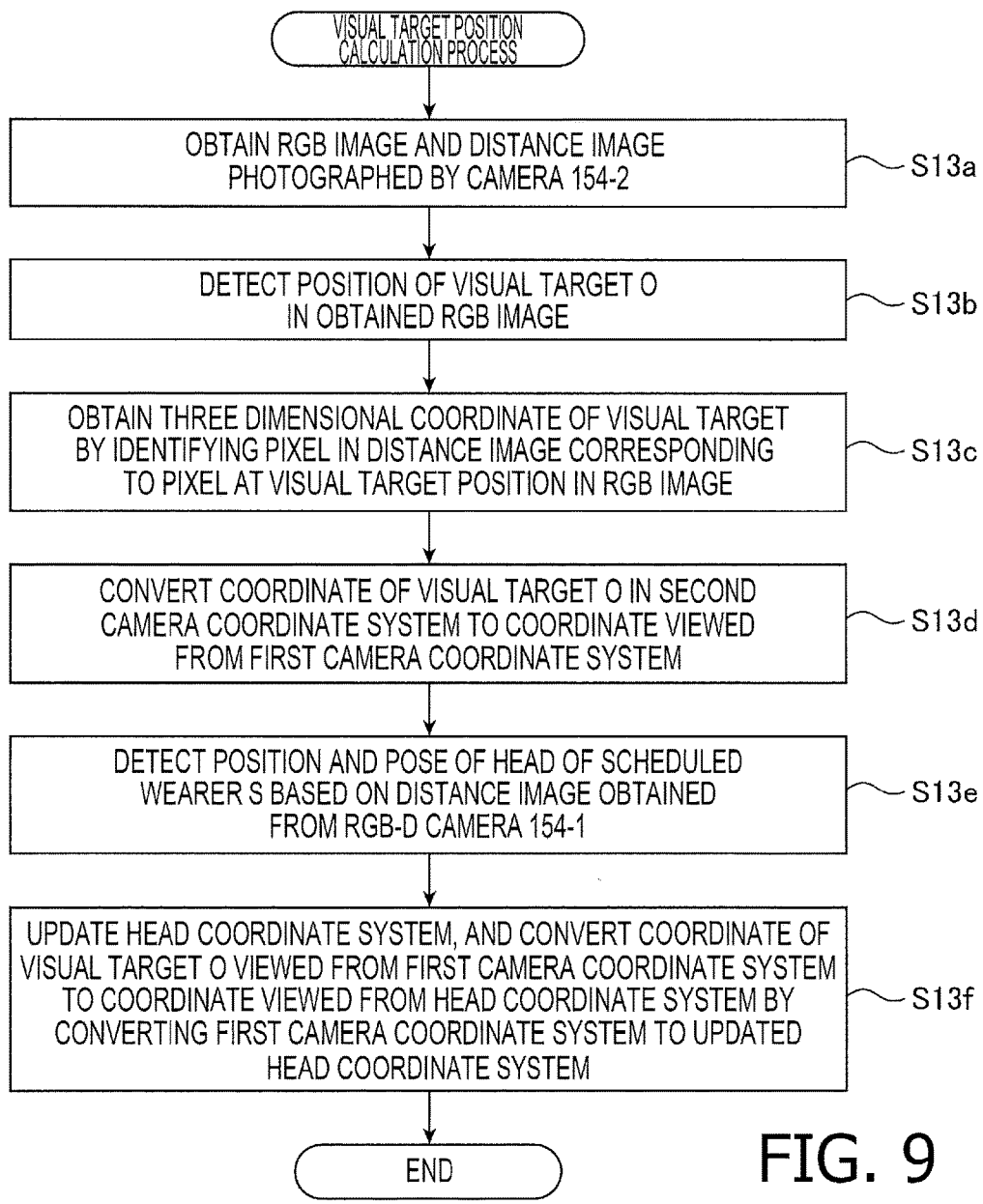
FIG. 9 is a flowchart illustrating step S3 (calculation process for visual target coordinate) in FIG. 5.

The scheduled wearer S is instructed to watch the visual target O during photographing. The scheduled wearer S may wear spectacle lenses which the scheduled wearer S usually wears. The visual target O is, for example, an object which moves randomly or regularly, or an object which appears or is arranged at a random position or a regular position. The processor 152a calculates the coordinate of the visual target O which is the end point of the visual line of the scheduled wearer S. It should be noted that the visual line information collected by the visual line information collecting apparatus 150 is vector information of a visual line, and includes a vector length and a unit vector of the visual line connecting the eyeball rotation center (the start point of the visual line) with the visual target O (the end point of the visual line). FIG. 9 is a flowchart illustrating in detail step S13.

Step S13a in FIG. 9

The processor 152a obtains the RGB image and the distance image photographed by the RGB-D camera 154-2 in step S11 (photographing process by RGB-D camera) in FIG. 5.

Step S13b in FIG. 9

The processor 152a detects the coordinate of the visual target O in the RGB image by analyzing the RGB image obtained by the RGB-D camera 154-2. For example, by using the known technique described in the non-patent document 2, the coordinate of the visual target O can be detected.

Step S13c in FIG. 9

The processor 152a identifies a pixel in the distance image corresponding to the coordinate (a pixel) detected in step S13b in FIG. 9. As a result, the three dimensional coordinate $v_{o1}$ of the visual target O is obtained.

Step S13d in FIG. 9

As described above, the start point (the eyeball rotation center) and the end point (the visual target) of the visual line are photographed by the different RGB-D cameras. In this case, the coordinate system of the RGB-D camera 154-2 is defined as having the origin at the optical center of the RGB-D camera 154-2, and is hereafter referred to as a "second camera coordinate system". As in the case of the first camera coordinate system, the second camera coordinate system has the X axis extending in the horizontal direction of the RGB-D camera 154-2, the Y axis extending in the vertical direction of the RGB-D camera 154-2, and the Z axis (the direction pointing to the front side of the RGB-D camera 154-2 is a plus direction) extending in the depth direction of the RGB-D camera 154-2.

In order to calculate the visual line information based on the start point and the end point of the visual line photographed by the separate RGB-D cameras having the different coordinate systems, it is necessary to convert the coordinate $v_{o2}$ of the visual target O in the second camera coordinate system to the coordinate $v_{o1}$ viewed from the first camera coordinate system, for example. When a rotation matrix and a translation vector obtained from a relative relationship (a relationship such as relative position or direction) of the first camera coordinate system viewed from the second camera coordinate system are defined as $R_{21}$ and $t_{21}$, respectively, and a time on a predetermined time axis is defined as t, the above described conversion process is expressed by the following equation:

$$v_{o1}{}^t = R_{21}{}^t(v_{o2}{}^t - t_{21}{}^t)$$

Let us consider, for example, a case where the relative positional relationship and the relative pose relationship between the RGB-D camera 154-1 and the RGB-D camera 154-2 are known values by installing the RGB-D camera 154-1 and the RGB-D camera 154-2 using a jig or the like. In this case, the rotation matrix $R_{21}$ and the translation vector $t_{21}$ can be treated as known parameters. Let us further consider a case where the relative positional relationship and the relative pose relationship between the RGB-D camera 154-1 and the RGB-D camera 154-2 are unknown. In this case, the same characteristic point (e.g., a characteristic point on the face of the scheduled wearer S) is measured by the RGB-D camera 154-1 and the RGB-D camera 154-2, and the relative positional relationship and the relative pose relationship of the RGB-D camera 154-1 and the RGB-D camera 154-2 are estimated based on the measured same characteristic point. It should be noted that since such estimation technique is known, detailed explanation thereof is omitted.

As described above, the coordinate system of the eyeball rotation center of the scheduled wearer S photographed by the RGB-D camera 154-1 has been converted to the head coordinate system. Therefore, the visual target O photographed by the RGB-D camera 154-2 should also be converted to the head coordinate system after being converted to the coordinate value viewed from the first camera coordinate system as in the case of the eyeball rotation center. In this case, the scheduled wearer S also moves his/her heads as well as the visual line because the scheduled wearer S chases the visual target O with his/her eyes. Therefore, the head coordinate system changes every second with respect to the first camera coordinate system. To chase change of the head coordinate system, the processor 152a detects the position and pose of the head of the scheduled wearer S based on the distance image obtained by the RGB-D camera 154-1 at predetermined time intervals.

S13f in FIG. 9

Each time the processor 152a detects the position and pose of the head of the scheduled wearer S, the processor 152a calculates the position difference and the pose difference of the head before and after the detection. The processor 152a updates the head coordinate system based on the calculated position difference and the pose difference of the head. By converting the first camera coordinate system to the updated head coordinate system, the processor 152a converts the coordinate $v_{o1}$ of the visual target viewed from the first camera coordinate system to the coordinate $v_{oh}$ of the visual target viewed from the head coordinate system. In other words, the processor 152a changes the coordinate of the visual target O by an amount corresponding to the position difference and the pose difference of the head before and after the detection so that the position and pose of the head is maintained before and after the detection in regard to processing on software (so that a state of pointing forward directly against the RGB-D camera 154-1 is maintained).

Supplement of S13 (calculation process for visual target coordinate) in FIG. 5

The explanation about the flowchart in FIG. 9 is based on the premise that the RGB-D camera 154-1 and the RGB-D camera 154-2 synchronously photograph the subject (the scheduled wearer S and the visual target O). However, the photographing timings of the two RGB-D cameras do not necessarily synchronized with each other on hardware. Therefore, by executing the following process, the photographing timings of the RGB-D camera 154-1 and the RGB-D camera 154-2 are synchronized with each other in regard to processing on software.

Figure 10:
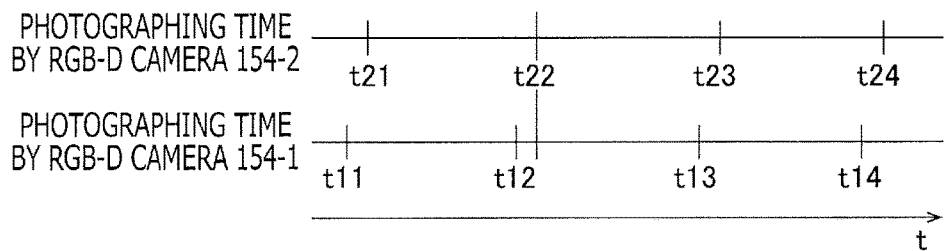
FIG. 10 illustrates an example of a time chart showing asynchronous photographing timing of two RGB-D cameras.

FIG. 10 is a time chart illustrating asynchronous photographing timing of the two RGB-D cameras. As shown in FIG. 10, for example, the photographing time t12 by the RGB-D camera 154-1 and the photographing time t22 by the RGB-D camera 154-2 are asynchronous with each other. The other corresponding photographing times are also asynchronous with each other. The photographing time is meta data of the RGB image and the distance image, and indicates a time at which the image is actually photographed by each RGB-D camera.

Let us consider, for example, a case where the coordinate $v_{o2}$ of the visual target O at the photographing time t22 is converted to the coordinate $v_{oh}$ of the visual target viewed from the head coordinate system. In this case, the processor 152a refers to the position and pose of the head of the scheduled wearer S at the photographing time t12 and the time difference between the photographing time t12 and the photographing time t22, and interpolates parameters of the position and pose of the head at the photographing time t22 by using an interpolation algorithm, such as smoothing spline. The interpolated values are estimated values of the position and pose of the head at the photographing time t22. The processor 152a then calculates the head coordinate system at the photographing time t22 from the estimated values, and converts the coordinate $v_{o1}$ of the visual target O at the photographing time t22 to the coordinate $v_{o1}$ of the visual target O viewed from the calculated head coordinate system. As a variation, the photographing timings of the RGB-D camera 154-1 and the RGB-D camera 154-2 may be synchronized by interpolating the coordinate $v_{o1}$ of the visual target O at the photographing time t12.

S14 in FIG. 5 (Calculation Process for Visual Line Information)

The processor 152a calculates the visual line vector having the eyeball rotation center coordinate $v_{rc1}$ ($x_h$, $y_h$, $z_h+\alpha$) calculated in step S12 (calculation process of eyeball rotation center coordinate) in FIG. 5 as the start point and the coordinate $v_{on}$ of the visual target O calculated in step S13 (calculation process for visual target coordinate) in FIG. 5 as the end point. The processor 152a stores the calculated visual line information in a predetermined area in the memory 152b. The visual line information includes the time axis information defined when the visual line is oriented to the visual target O (e.g., time information, specifically the photographing time by the RGB-D camera 154-1 and the RGB-D camera 154-2).

S15 in FIG. 5 (Termination Judgment Process)

The processor 152a judges whether or not the visual line information corresponding to a predetermined time (a predetermined number of pieces of information) has been collected (stored) in the memory 152b. When the processor 152a judges that the visual line information corresponding to the predetermined time has been collected (S15 in FIG. 5: YES), the process of the flowchart is terminated. When the processor 152a judges that the visual line information corresponding to the predetermined time has not been collected (S15 in FIG. 5: NO), the process returns to step S13 (calculation process for visual target coordinate) in FIG. 5.

After collecting the visual line information corresponding to the predetermined time (after step S15: YES), the processor 152a may display information concerning the visual line information on the monitor 152d. Various types of displaying manners for displaying information concerning the visual line information can be considered. For example, frequency of visual line passing points may be displayed on an image of a lens cut in a shape of a frame, for example, by contour lines, shading or dots.

According to the example 1, the start point of the visual line is set at the eyeball rotation center which is equal to the origin defined for design of the spectacle lens. Therefore, an error in the direction and distance of the visual line caused by a shift between the origin used for design of the spectacle lens and the start point of the visual line does not occur. Accordingly, the visual line information collected according to the example 1 is suitable for use for design of the spectacle lens. Furthermore, according to the example 1, the scheduled wearer S is photographed by the RGB-D camera 154-1 placed before the eyes of the scheduled wearer S. Since the scheduled wearer S is photographed largely in the RGB image, it is possible to detect the two dimensional position of the eye by the RGB image with a high degree of accuracy. Furthermore, since the RGB-D camera 154-1 and the scheduled wearer S are close to each other, it is possible to detect the position of the eye in the depth direction with a high degree of accuracy. It is also possible to detect the position and pose of the head of the scheduled wearer S with a high degree of accuracy. As described above, according to the example 1, since the position and pose of the eye and the head of the scheduled wearer S can be detected with a high degree of accuracy, the calculation accuracy of the visual line is enhanced. Therefore, the visual line information which is advantageously used for design of spectacle lenses can be obtained.

Example 2

Configuration of Visual Line Information Collecting Apparatus 150M

Figure 11:
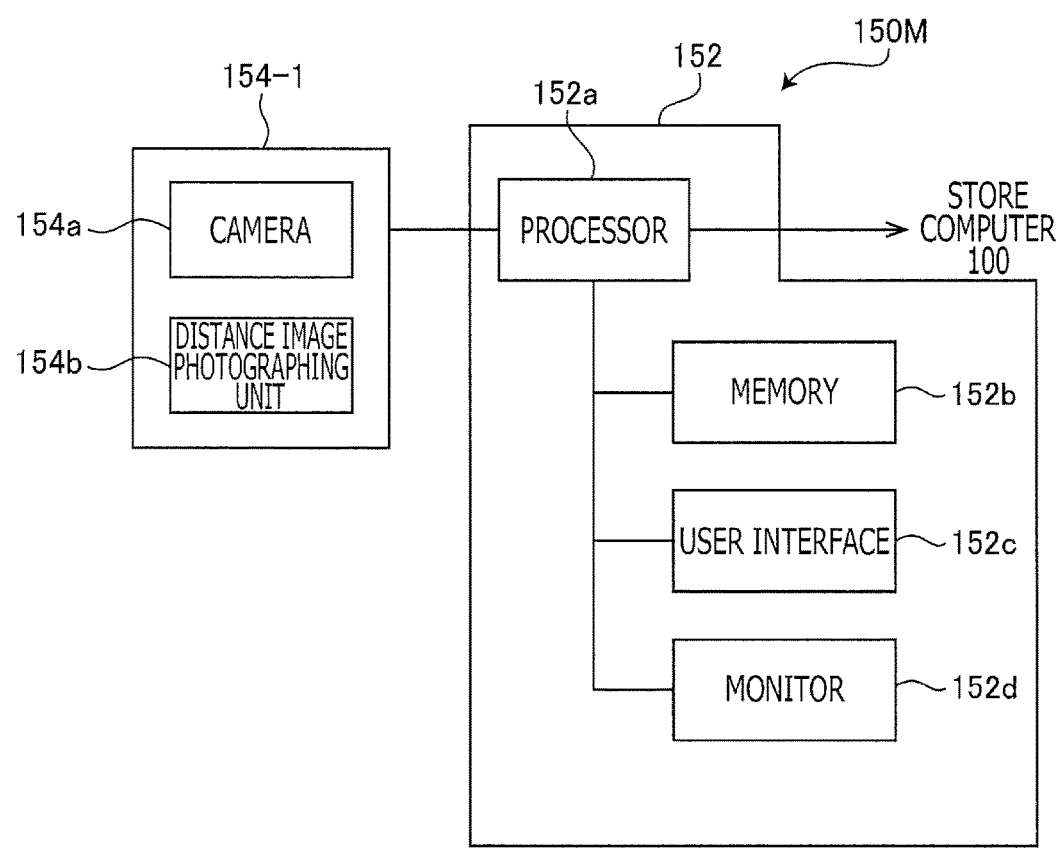
FIG. 11 is a block diagram illustrating a configuration of a visual line information collecting apparatus according to an example 2 of the invention.

FIG. 11 is a block diagram illustrating a configuration of a visual line information collecting apparatus 150M according to the example 2. As show in FIG. 11, the visual line information collecting apparatus 150M includes the information processing terminal 152 and the RGB-D camera 154-1. That is, in contrast to the visual line information collecting apparatus 150 according to the example 1, the visual line information collecting apparatus 150M includes only one RGB-D camera. In the example 2, explanations overlapping with those of the example 1 are omitted or simplified for the sake simplicity. In the example 2, to configurations and steps which are the same as those of the example 1, the same reference numbers are assigned and explanations thereof are omitted or simplified.

Figure 12:
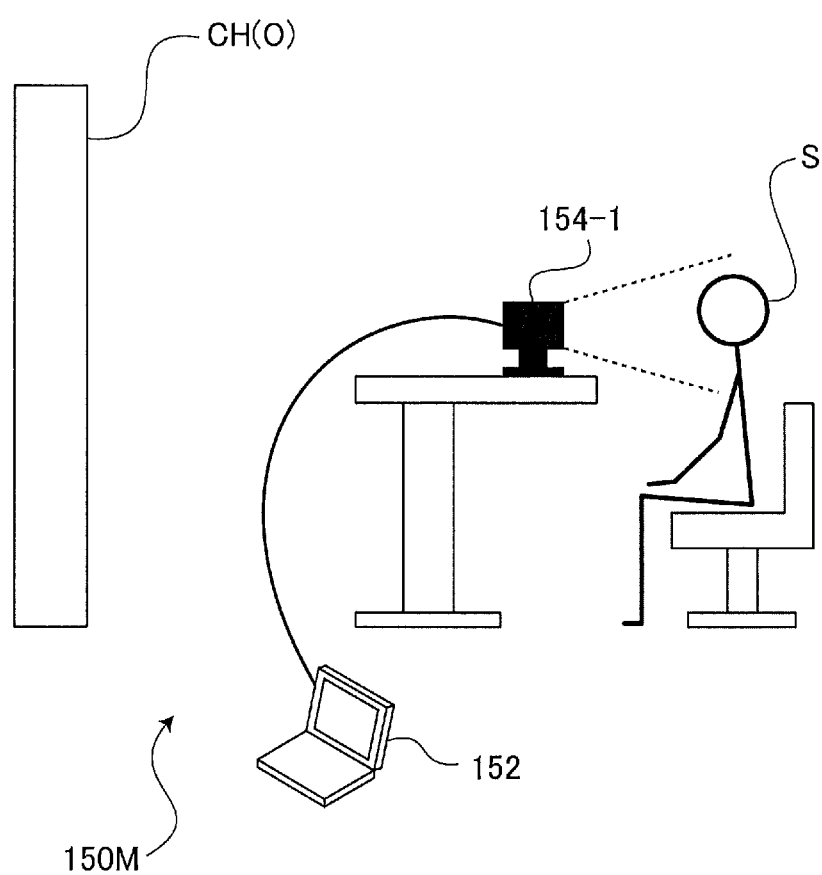
FIG. 12 illustrates a use condition of the visual line information collecting apparatus according to the example 2 of the invention.
Figure 13:
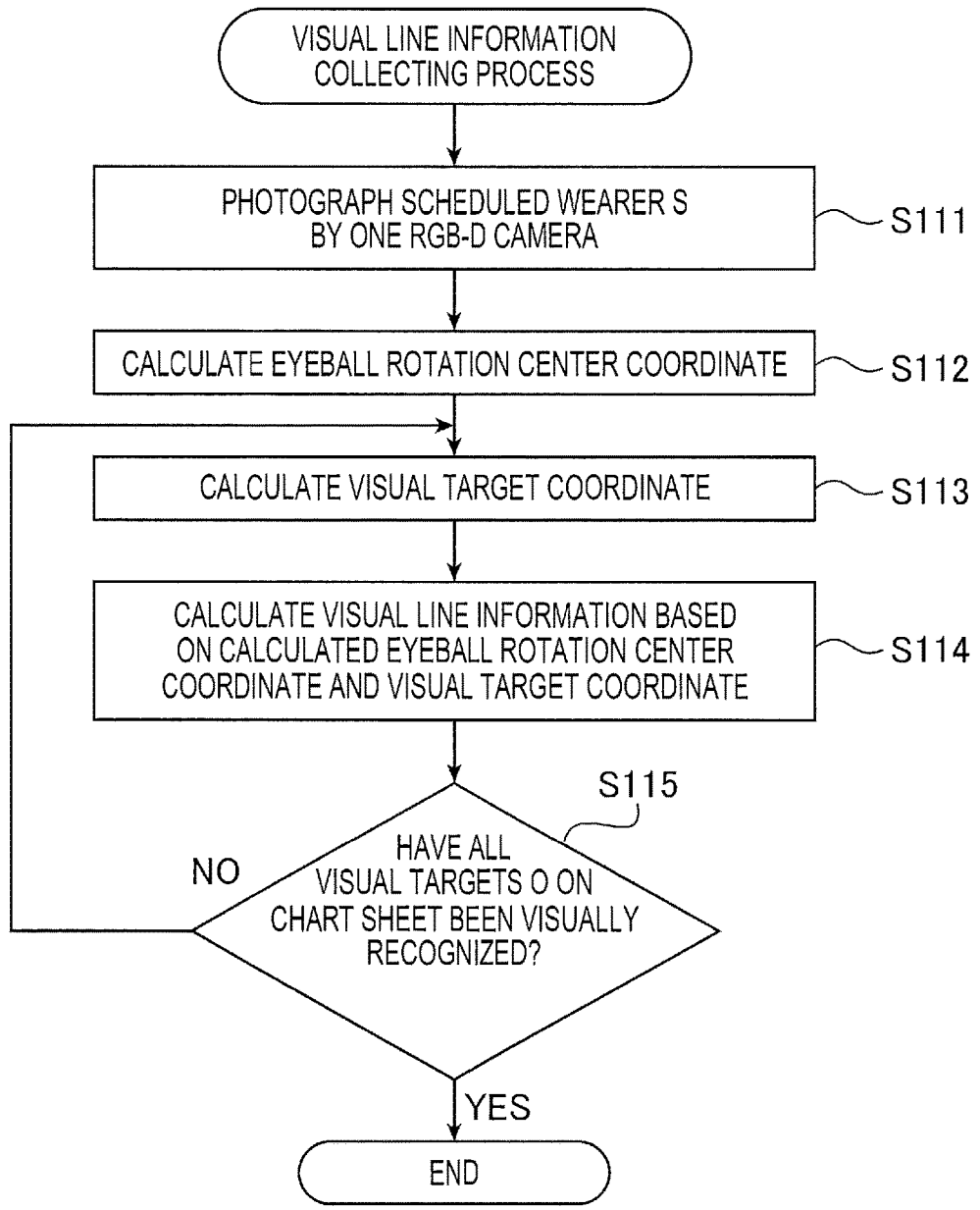
FIG. 13 is a flowchart illustrating a visual line information collecting process according to the example 2 of the invention.

FIG. 12 illustrates a use condition of the visual line information collecting apparatus 150M according to the example 2. FIG. 13 is a flowchart illustrating a visual line information collecting process by the visual line information collecting apparatus 150M used in the use condition shown in FIG. 12. As shown in FIG. 12, at a position farther from the RGB-D camera 154-1 viewed from the scheduled wearer S and on the rear side of the RGB-D camera 154-1, a chart sheet CH is installed. On the chart sheet CH, a plurality of visual targets O are printed at various positions.

Visual Line Information Collecting Process by Visual Line Information Collecting Apparatus 150M S111 in FIG. 13 (Photographing Process by RGB-D Camera)

The RGB-D camera 154-1 photographs an RGB image and a distance image of the scheduled wearer S at a predetermined frame rate.

S112 in FIG. 13 (Calculation Process of Eyeball Rotation Center Coordinate) The processor 152a calculates the coordinate $v_{rc1}$ of the eyeball rotation center which is the start point of the visual line of the scheduled wearer S. Since step S112 is the same as step S12 (calculation process of eyeball rotation center coordinate) in FIG. 5, further explanation thereof is omitted.

S113 in FIG. 13 (Obtaining Process for Visual Target Coordinate)

During the photographing, the scheduled wearer S visually recognizes each visual target O on the chart sheet CH in accordance with, for example, voice guidance output from the information processing terminal 152. The position of each visual target O on the chart sheet CH is known, and the position information has been stored in the memory 152b of the information processing terminal 152. The processor 152a reads the position information of the visual target O corresponding to the voice guidance from the memory 152b as the coordinate $v_{o1}$ of the visual target O viewed from the first camera coordinate system, and, as in the case of step S13f in FIG. 9, converts the coordinate $v_{oi}$ to the coordinate $v_{oh}$ of the visual target viewed from the head coordinate system.

S114 in FIG. 13 (Calculation Process for Visual Line Information)

The processor 152a calculates the visual line vector (including a vector length and a unit vector) having the eyeball rotation center coordinate $v_{rc1}$ ($x_h$, $y_h$, $z_h+\alpha$) calculated in step S112 (calculation process of eyeball rotation center coordinate) in FIG. 13 as the start point and the coordinate $v_{oh}$ of the visual target O calculated in step S113 (obtaining process for visual target coordinate) in FIG. 13 as the end point. The processor stores the calculated visual line information in a predetermined area in the memory 152b.

S115 in FIG. 13 (Termination Judgment Process)

By detecting the end of the voice guidance, the processor 152a judges whether or not the scheduled wearer S has visually recognized all the visual targets O on the chart sheet CH. When the processor 152a judges that the scheduled wearer S has visually recognized all the visual targets O on the chart sheet CH (S115: YES in FIG. 13), the processor 152a terminates the flowchart while judging that the visual line information corresponding to the predetermined time has been collected. When the processor 152a judges that there is a visual target O which the scheduled wearer S has not visually recognized yet (S115: NO in FIG. 13), the process returns to step S113 (obtaining process for visual target coordinate) in FIG. 13 while judging that the visual line information corresponding to the predetermined time has not been collected.

As in the case of the example 1, according to the example 2, since the start point of the visual line is set at the eyeball rotation center which is equal to the origin for design of the spectacle lens, the visual line information collected according to the example 2 is suitable for use of design of the spectacle lens. Furthermore, as in the case of the example 1, according to the example 2, since the scheduled wearer S is photographed by the RGB-D camera 154-1 placed before the eyes of the scheduled wearer S, the visual line information which is advantageously used for design of the spectacle lens can be obtained with a high degree of accuracy. Furthermore, according to the example 2, since a single RGD-B camera 154-1 is sufficient, cost for the visual line information collecting apparatus 150M can be reduced.

Variation 1 of Examples 1 and 2

In the examples 1 and 2, the three dimensional coordinate of the corneal apex is identified using the RGB-D camera. Specifically, in the examples 1 and 2, a method, where the corneal apex coordinate (a pixel) is identified using the RGB image by the camera 154a, and then the three dimensional coordinate of the corneal apex is identified from the pixel in the distance image by the distance image photographing unit 154b corresponding to the pixel of the identified corneal apex, is used. On the other hand, in the variation 1, a corneal apex coordinate can be directly identified from a distance image without using an RGB image by applying the technique described in non-patent document 4 (Tae Kyun Kim, Seok Cheol Kee and Sang Ryong Kim: "Real-Time Normalization and Feature Extraction of 3D Face Data Using Curvature Characteristics"). Furthermore, regarding the visual target O, when an object having a characteristic shape is used as the visual target, the coordinate of the visual target O can be directly identified from the distance image without using the RGB image by applying the technique described in the non-patent document 4. Since, in the variation 1, it is possible to replace the RGB-D camera with a distance image sensor, cost of the visual line information collecting apparatus can be suppressed.

Variation 2 of Examples 1 and 2

Figure 15:
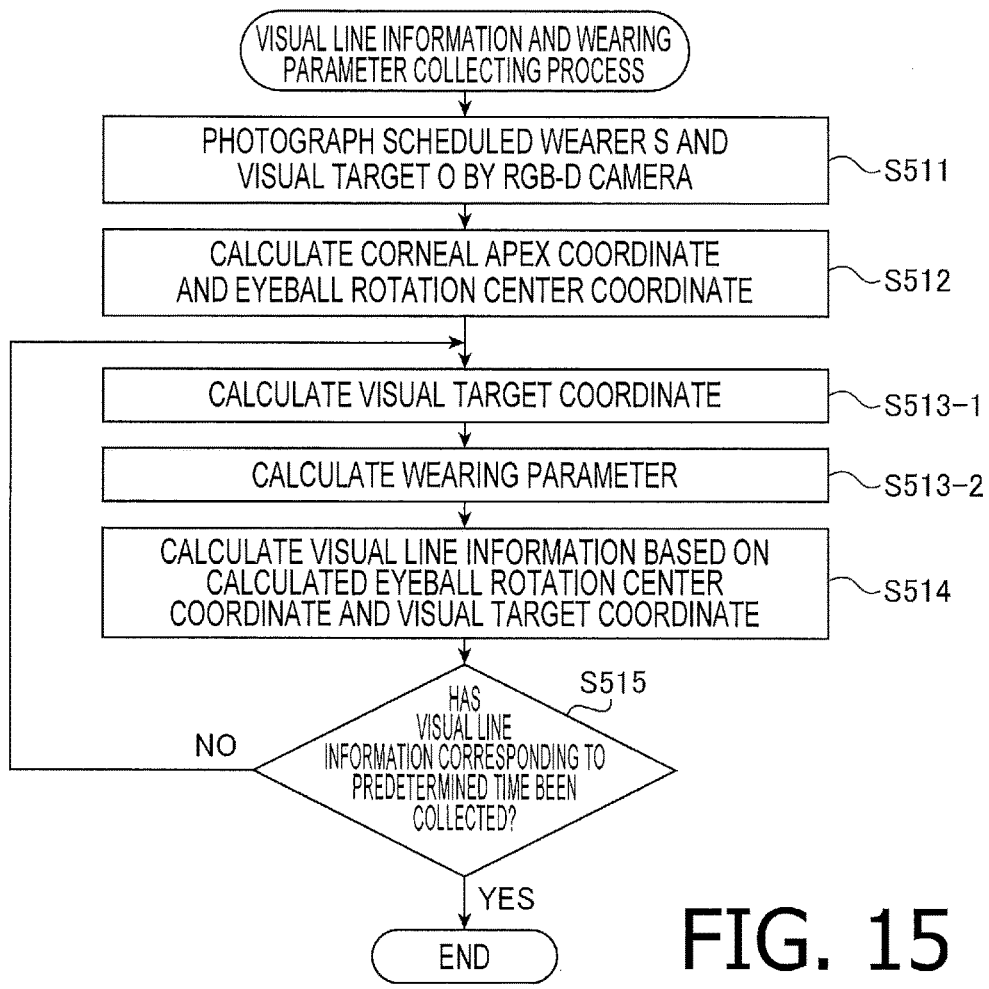
FIG. 15 is a flowchart illustrating a visual line information and wearing parameter collecting process by the visual line information collecting apparatus according to the example 3 of the invention.

In the example 1, a role of the RGB-D camera 154-1 after execution of step S12 (calculation process of eyeball rotation center coordinate) in FIG. 15 is limited to estimating the position and pose of the head of the scheduled wearer S. As in the case of the example 1, also in the example 2, a role of the RGB-D camera 154-1 after execution of step S112 (calculation process of eyeball rotation center coordinate) in FIG. 13 is limited to estimating the position and pose of the head of the scheduled wearer S. For this reason, in the variation 2, after the eyeball rotation center coordinate is calculated in step S12 in FIG. 5 or in step S112 in FIG. 13, the process executed by the RGB-D camera 154-1 may be substituted by an IMU (Inertial Measurement Unit). Specifically, in the variation 2, the scheduled wearer S wears the IMU on the head. In the variation 2, steps after S13 (calculation process for visual target coordinate) in FIG. 5 or steps after S113 (obtaining process for visual target coordinate) in FIG. 13 are executed using the position and pose of the head measured by the IMU. It should be noted that in this case the origin of the head coordinate system is set at the barycenter of the IMU.

Example 3

In the following, the example 3 regarding a visual line information collecting process is explained. As explained in detail below, in the example 3, wearing parameters are collected simultaneously and in series with the visual line information while considering the pose of the head of the scheduled wearer S. It should be noted that, in the example 3, explanations overlapping with those of the example 1 are omitted or simplified. Furthermore, in the example 3, to configurations and steps which are substantially the same as those of the example 1, the same reference numbers are assigned and explanation thereof is omitted or simplified.

Figure 14:
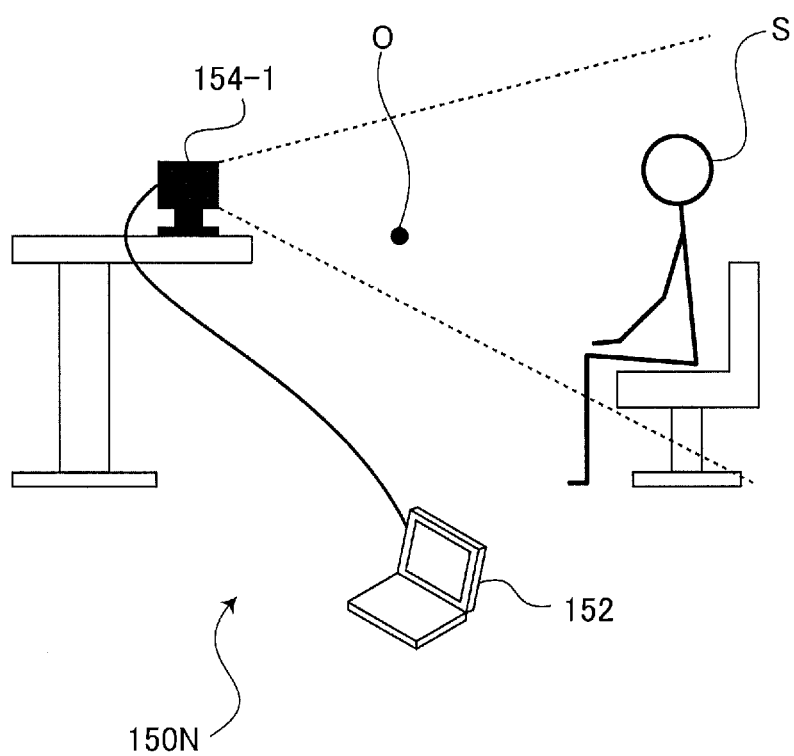
FIG. 14 illustrates a use condition of a visual line information collecting apparatus according to an example 3 of the invention.

FIG. 14 illustrates a use condition of a visual line information collecting apparatus 150N according to the example 3. Since the configuration of the visual line information collecting apparatus 150N of the example 3 is the same as the configuration (FIG. 11) in the example 2, explanation thereof is omitted. As shown in FIG. 14, the visual line information collecting apparatus 150N according to the example 3 includes the information processing apparatus 152 and the RGB-D camera 154-1, and the RGB-D camera 154-1 is installed on a table so that the visual target O and the scheduled wearer S can be photographed. That is, in the example 3, the visual line information taking into account the pose of the head and the wearing parameters are obtained by a single RGB-D camera. FIG. 15 is a flowchart illustrating a visual line information and wearing parameter collecting process by the visual line information collecting apparatus 150N.

Visual Line Information and Wearing Parameter Collecting Process by Visual Line Information Collecting Apparatus 150N FIG. 15 (Photographing Process by RGB-D Camera)

The RGB-D camera 154-1 photographs an RGB image and a distance image of the scheduled wearer S and the visual target O at a predetermined frame rate. S512 in FIG. 15 (Calculation Process of Corneal Apex and Eyeball Rotation Center Coordinate)

The processor 152a calculates the coordinate $v_{rc1}$ of the eyeball rotation center which is the start point of the visual line of the scheduled wearer S, and holds the calculated coordinate. Since step S512 is similar to step S12 (calculation process of eyeball rotation center coordinate) in FIG. 5, further explanation thereof is omitted. In step S512, the corneal apex coordinate measured for obtaining the eyeball rotation center is also held. Specifically, since the corneal apex coordinates are obtained for an amount corresponding to the predetermined number of frames, the average of the obtained corneal apex coordinates is determined and held as the corneal apex coordinate. The held corneal apex coordinate is used for calculating the wearing parameters in a later stage.

S513-1 in FIG. 15 (Obtaining Process for Visual Target Coordinate)

The scheduled wearer S is instructed to watch the visual target O during the photographing. In order to watch the visual target O, the scheduled wearer S may watch the visual target with the naked eyes or may use spectacle lenses which the scheduled wearer S usually wears. However, when, of the wearing parameters, one of a frame vertex distance, a frame pantoscopic angle and a frame face form angle is calculated in step S513-2, the scheduled wearer S is required to wear the spectacle lenses. The visual target O is, for example, an object which moves randomly or regularly, or an object which appears or is arranged at a random position or a regular position. The processor 152a calculates the coordinate of the visual target O which is the end point of the visual line of the scheduled wearer S. Since the obtaining process of the coordinate of the visual target O is the same as step S13 in FIG. 5, explanation thereof is omitted.

S513-2 in FIG. 15 (Calculation Process of Wearing Parameter)

The processor 152 calculates the wearing parameters (a frame pantoscopic angle, a frame face form angle, a frame vertex distance and a pupillary distance) (only a near working distance is calculated in S514). Details of the wearing parameters are explained below.

Calculation Process of Frame Pantoscopic Angle

Figure 16:
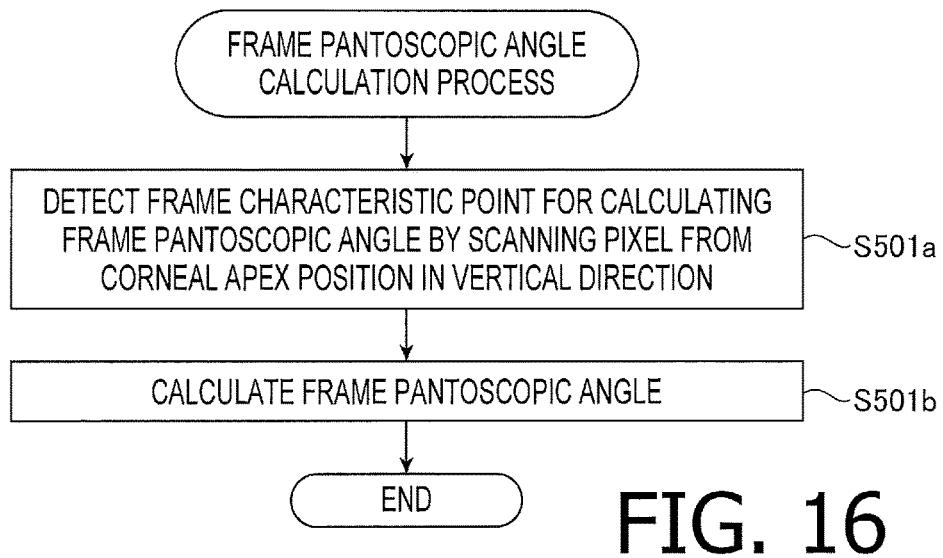
FIG. 16 is a flowchart illustrating a frame pantoscopic angle calculation process according to the example 3 of the invention.

FIG. 16 is a flowchart illustrating a frame pantoscopic angle calculation process. In this process, frontal face three dimensional data of the scheduled wearer S defined based on the position and pose of the head obtained in step S513-1 in FIG. 15 and the corneal apex coordinate (the corneal apex coordinate obtained in a state of not wearing the spectacle lenses) held in step S512 are used.

Step S501a in FIG. 16

Figure 17:
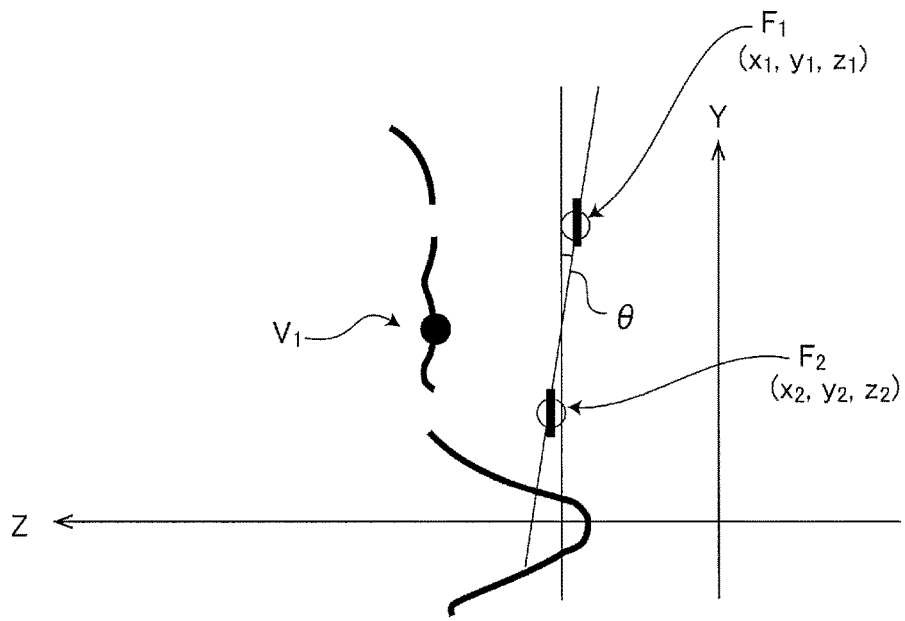
FIG. 17 is a transversal cross sectional view of a frontal face three dimensional data, and is used for explaining the frame pantoscopic angle calculation process.

FIG. 17 is a transversal cross sectional view of the frontal face three dimensional data, and is used for explaining the frame pantoscopic angle calculation process. FIG. 17 indicates the corneal apex coordinate $V_1$ as well as the transversal cross section of the frontal face three dimensional data. The processor 152a scans the pixels in the vertical direction from the corneal apex coordinate $V_1$, and detects a point at which the Z coordinate value discontinuously changes rapidly as a frame characteristic point. Through this scanning, the positions $F_1$ ($x_1$, $y_1$, $z_1$) and $F_2$ ($x_2$, $y_2$, $z_2$) shifted in the Z axis direction from the face are detected as the frame characteristic points.

Step S501b in FIG. 16

The processor 152a calculates the frame pantoscopic angle using the positions $F_1$ and $F_2$ of the frame characteristic points thus detected. The frame pantoscopic angle ($\theta$) is expressed as follows.

$$\text{frame pantoscopic angle}) = \tan^{-1}\left(\frac{z_2 - z_1}{y_1 - y_2}\right)$$

Calculation Process for Frame Face Form Angle

Figure 18:
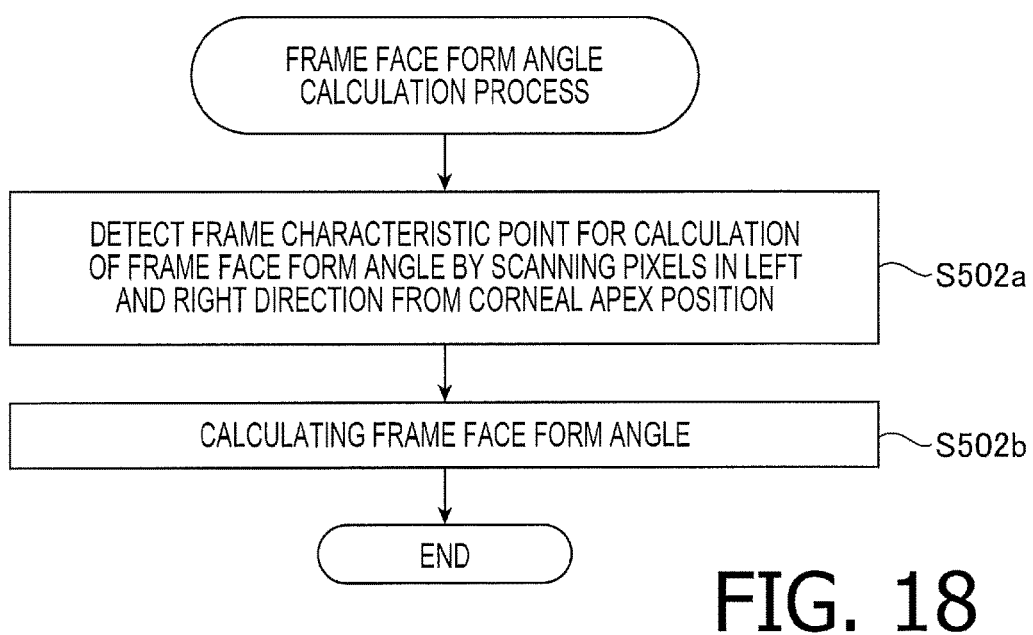
FIG. 18 is a flowchart illustrating a frame face than angle calculation process according to the example 3 of the invention.

FIG. 18 is a flowchart illustrating a frame face form angle calculation process. In this process, frontal face three dimensional data of the scheduled wearer S defined based on the position and pose of the head obtained in step S513-1 in FIG. 15 and the corneal apex coordinate held in step S512 are used.

Step S502a in FIG. 18

Figure 19:
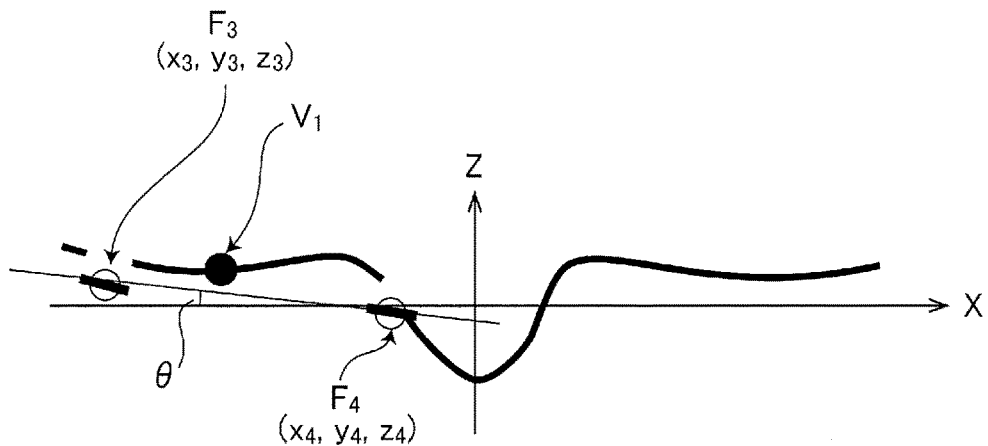
FIG. 19 is a top cross sectional view of the frontal face three dimensional data, and is used for explaining the frame face form angle calculation process.

FIG. 19 is a top cross sectional view of the frontal face three dimensional data, and is used for explaining the frame face form angle calculation process. FIG. 19 indicates the corneal apex coordinate $V_1$ as well as the top cross section of the frontal face three dimensional data. The processor 152a scans the pixels in the left and right direction from the corneal apex coordinate $V_1$, and detects a point at which the Z coordinate value discontinuously changes rapidly as a frame characteristic point. Through this scanning, the positions $F_3$ ($x_3$, $y_3$, $z_3$) and $F_4$ ($x_4$, $y_4$, $z_4$) shifted in the Z axis direction from the face are detected as the frame characteristic points.

Step S502b in FIG. 18

The processor 152a calculates the frame face form angle using the positions $F_3$ and $F_4$ of the frame characteristic points thus detected. The frame face form angle ($\theta$) is expressed as follows.

$$\text{frame face form angle}) = \tan^{-1}\left(\frac{z_3 - z_4}{x_4 - x_3}\right)$$

Calculation Process for Frame Vertex Distance

Figure 20:
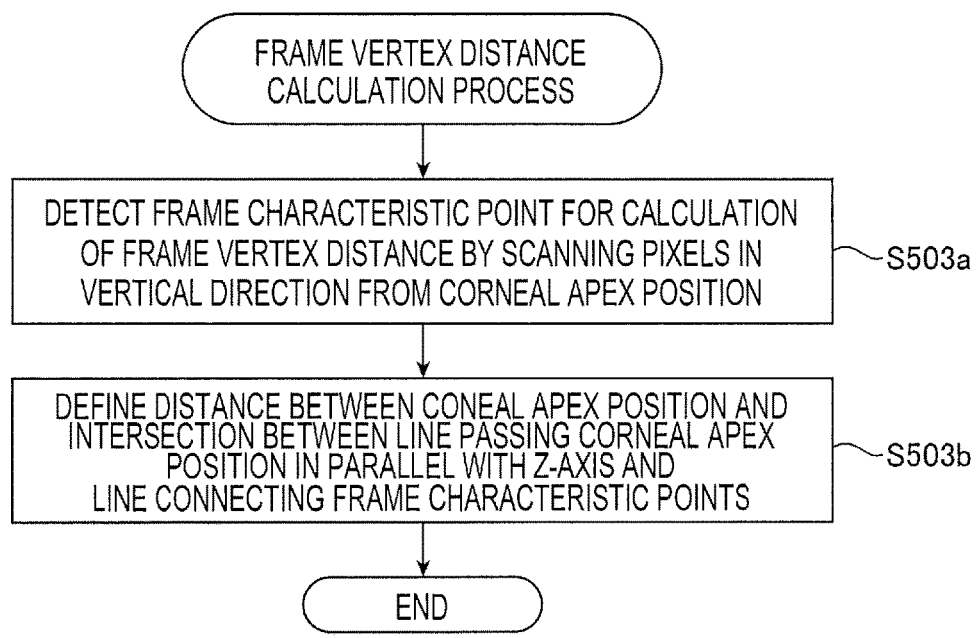
FIG. 20 is a flowchart illustrating a frame vertex distance calculation process according to the example 3 of the invention.

FIG. 20 is a flowchart illustrating a frame vertex distance calculation process. In this process, frontal face three dimensional data of the scheduled wearer S defined based on the position and pose of the head obtained in step S513-1 in FIG. 15 and the corneal apex coordinate held in step S512 are used.

Step S503a in FIG. 20

Figure 21:
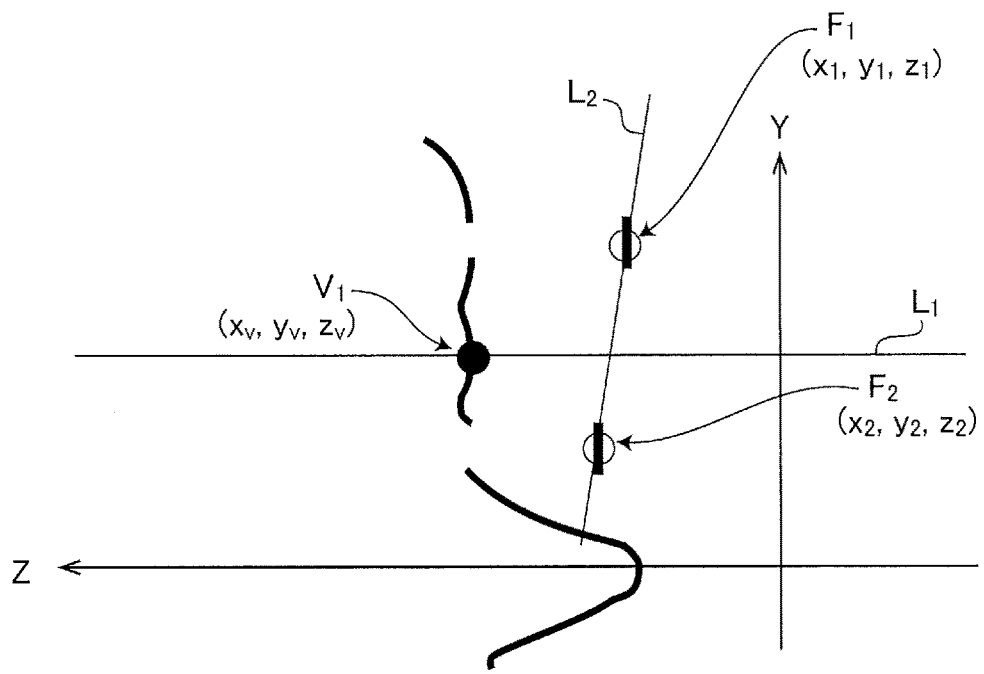
FIG. 21 is a transversal cross sectional view of the frontal face three dimensional data, and is used for explaining the frame vertex distance calculation process.

FIG. 21 is a transversal cross sectional view of the frontal face three dimensional data, and is used for explaining the frame vertex distance calculation process. FIG. 21 indicates the corneal apex coordinate $V_1$ and the frame characteristic points $F_1$ and $F_2$, as well as the transversal cross section of the frontal face three dimensional data. As in the case of step S501a in FIG. 16, the processor 152a calculates the positions $F_1$ and $F_2$ of the frame characteristic points.

Step S503b in FIG. 20

In FIG. 21, a line $L_1$ is a line drawn in parallel with the Z axis from the corneal apex $V_1$, and a line L2 is a line connecting the frame characteristic points $F_1$ and $F_2$. The processor 152a calculates the distance between the corneal apex $V_1$ and an intersection of the line $L_1$ and the line $L_2$ as the frame vertex distance.

Calculation Process of Pupillary Distance

Figure 22:
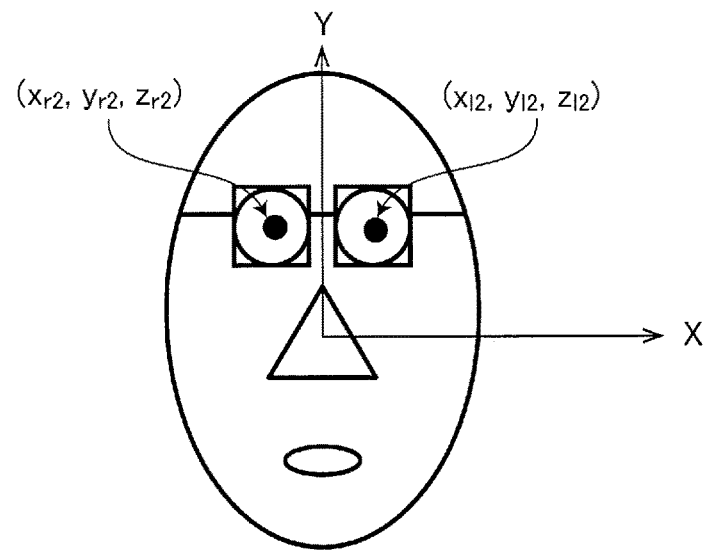
FIG. 22 is a front view of the frontal face three dimensional data, and is used for explaining a pupillary distance calculation process.

FIG. 22 is a front view of the frontal face three dimensional data, and is used for explaining the pupillary distance calculation process. The processor 152a calculates the pupillary distance by calculating $x_{12}$-$x_{12}$ along the X axis using the corneal apex positions (($x_{r2}$, $y_{r2}$, $z_{r2}$) and ($x_{12}$, $y_{12}$, $z_{12}$)) of the left and right eyes obtained in step S512 in FIG. 15.

S514 in FIG. 15 (Calculation Process for Visual Line Information) The processor 152a calculates the visual line vector having the eyeball rotation center coordinate $v_{rc1}$ ($x_h$, $y_h$, $z_h+\alpha$) calculated in step S512 (calculation process of eyeball rotation center coordinate) in FIG. 15 as the start point and the coordinate $v_{oh}$ of the visual target O calculated in step S513-1 (calculation process for visual target coordinate) in FIG. 15 as the end point. The processor 152a stores the calculated visual line information in a predetermined area in the memory 152b. The visual line information includes the time axis information defined when the visual line is oriented to the visual target O (e.g., time information, specifically the photographing time by the RGB-D camera 154-1). Regarding the near working distance, the near working distance can be calculated by regarding the vector length defined in a state where the visual target O is installed at a distance corresponding to the near work of the scheduled wearer S as the near working distance.

S515 in FIG. 15 (Termination Judgment Process)

The processor 152a judges whether or not the visual line information corresponding to a predetermined time (a predetermined number of pieces of information) has been collected (stored) in the memory 152b. When the processor 152a judges that the visual line information corresponding to the predetermined time has been collected (S515 in FIG. 15: YES), the process of the flowchart is terminated. When the processor 152a judges that the visual line information corresponding to the predetermined time has not been collected (S515 in FIG. 15: NO), the process returns to step S513-1 (calculation process for visual target coordinate) in FIG. 15.

As in the case of the examples 1 and 2, according to the example 3, the start point of the visual line is set at the eyeball rotation center which is equal to the origin defined for design of the spectacle lens. Therefore, the visual line information collected according to the example 3 is suitable for use for design of the spectacle lens. Furthermore, the visual line information (direction and distance) is measured continuously as time series data. Therefore, it is possible to judge which part of the lens the scheduled wearer S uses with high frequency, and thereby it becomes possible to give suitable aberration distribution to the lens based on the judged use frequency.

According to the example 3, the wearing parameters are obtained simultaneously and continuously as the time series data. Therefore, it becomes possible to collect the wearing parameters with a high degree of reliability by using an average or a median for the wearing parameters obtained as the time series data (there parameters are defined as true wearing parameters). According to the example 3, the visual line information and the wearing parameters are obtained simultaneously and as time series data with a simple configuration as shown in FIG. 14 as an example. Furthermore, according to the example 3, the pose of the head is considered for the calculation process of the wearing parameters. Therefore, accurate wearing parameters can be obtained.

The configuration of the visual line information collecting apparatus is not limited to that shown in FIG. 14, but various types of configurations may be used. For example, the configuration in which two RGB-D cameras are used may also realize the same process as that described in the example 3.

Figure 23:
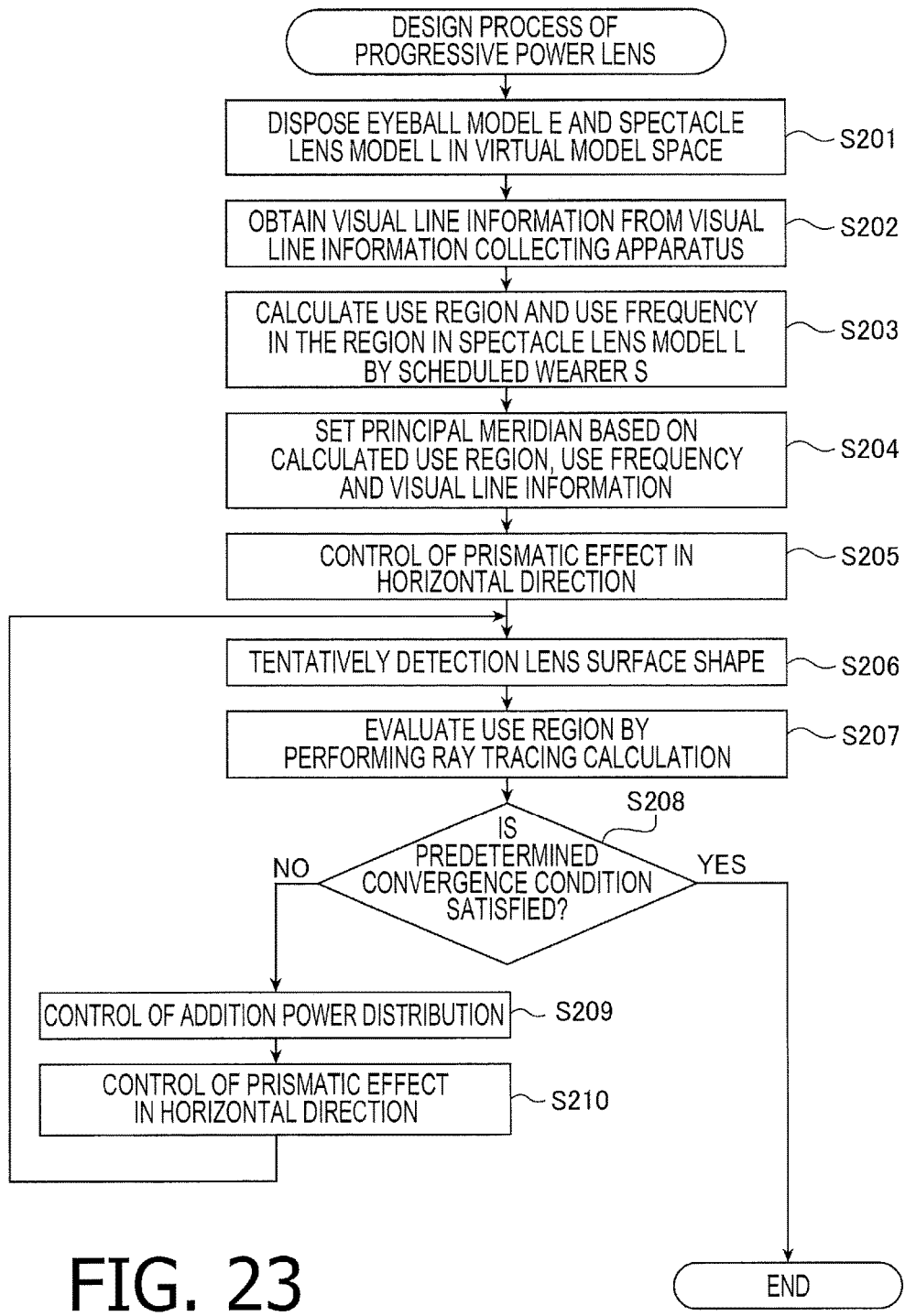
FIG. 23 is a flowchart illustrating a progressive lens design process by a spectacle lens design computer.

Specific Design Method of Spectacle Lens by Spectacle Lens Design Computer 202 Hereafter, a method for designing spectacle lenses using the visual line information collected according to the example 1 or 2 is explained. FIG. 23 is a flowchart illustrating a progressive power lens design process by the spectacle lens design computer 202.

Design Example of Progressive Power Lens

S201 in FIG. 23 (Construction of Virtual Model)

Figure 24:
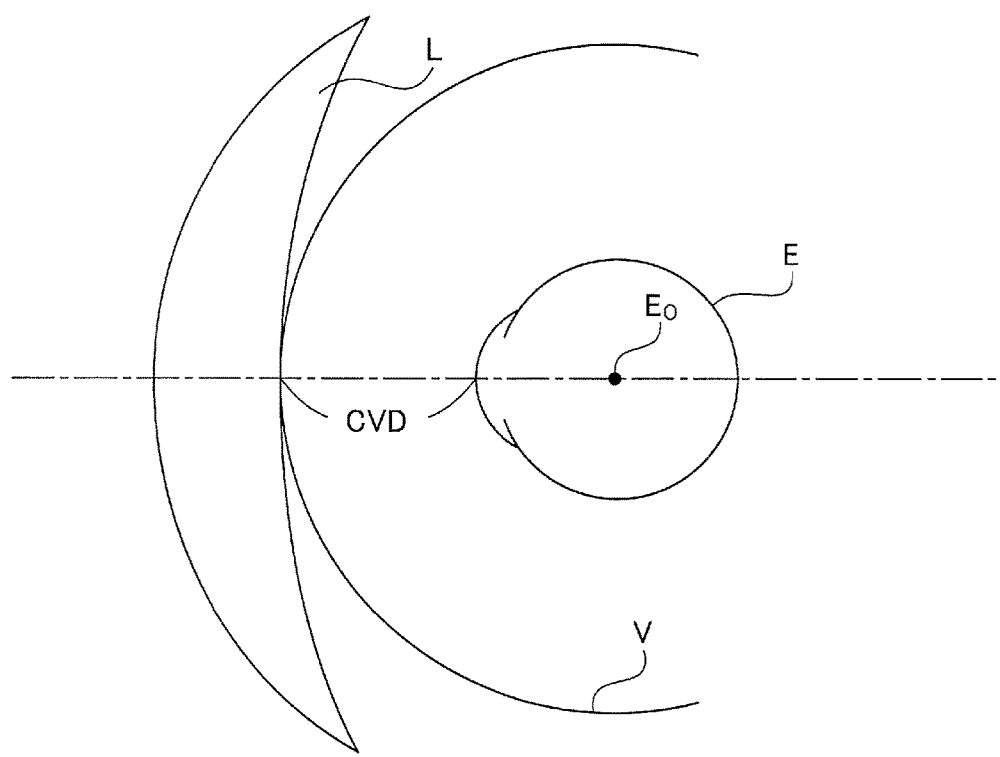
FIG. 24 illustrates an example of a virtual model constructed by the spectacle lens design computer.

The spectacle lens design computer 202 constructs a predetermined virtual model including an eyeball and a spectacle lens, assuming a state where the scheduled wearer S wears spectacle lenses. FIG. 24 illustrates an example of the virtual model constructed by the spectacle lens design computer 202.

The eye axis length of an eyeball differs between myopia and hyperopia. For this reason, the spectacle lens design computer 202 has stored in advance information indicating how the eye axis length differs depending on degrees of myopia and hyperopia. From this information, the spectacle lens design computer 202 selects a suitable eyeball model E in accordance with the prescription (spherical power, cylindrical power) of the scheduled wearer S contained in the received ordering data, and disposes a selected eyeball model E in a virtual model space. An eyeball rotation center Eo is defined at the center of the eyeball model E.

The spectacle lens design computer 202 designs an initial spectacle lens model L while defining the eyeball rotation center Eo as the origin. Specifically, the spectacle lens design computer 202 determines the shape of each of the outer surface (the convex surface) and the inner surface (the concave surface) of the lens to be one of a spherical surface, an aspherical surface, a progressive surface and a free-form surface (other than a progressive surface) based on the prescription contained in the received ordering data. For example, in the case of a one side progressive power lens, the convex surface or the concave surface is determined to be the progressive surface. The spectacle lens design computer 202 designs the initial spectacle lens model L by determining the center thickness based on the prescription, the refractive index of the lens and the like, and disposing the convex surface and the concave surface while securing an interval corresponding to the determined center thickness.

Based on the wearing parameters measured trough the flowchart in FIG. 15, the spectacle lens design computer 202 converts the measurements of the frame to lens arrange parameters, such as, a lens face form angle, a lens pantoscopic angle, and a corneal vertex distance CVD. Such conversion is performed using the measured wearing parameters, a shape, a rim and a groove position of a frame, a dioptric power, a base curve, a fitting point and a thickness of a lens, and the like. Based on the obtained lens face form angle, the lens pantoscopic angle, and the corneal vertex distance CVD, the spectacle lens model L is disposed for the eyeball model E. When the measurements of the wearing parameters are not available, arbitrary values may be designated, and the lens arrangement parameters may be calculated from the designated values. The corneal vertex distance CVD is a distance between the rear vertex of the spectacle lens model L and the corneal apex of the eyeball model E. The fitting point is determined depending on how long (mm) the pupil center shifts upward or downward from a datum line or how long (mm) the pupil center shifts upward from a lower rim of a frame when a half of a B size in a box system defined in a JIS (Japanese Industrial Standard) is regarded as a reference line (the datum line). When the above described various parameters are unknown, standard values may be used as the lens arrangement parameters. As an example, the corneal vertex distance CVD may be a default value (e.g., 12.5 mm).

S202 in FIG. 23 (Obtaining of Visual Line Information)

The spectacle lens design computer 202 obtains the visual line information collected according to the example 1 (or the example 2) from the visual line information collecting apparatus 150 (or 150M). As described above, the obtained visual line information includes the information concerning the visual line vector, such as the vector length and a unit vector, and the time axis information when the visual line is oriented to the visual target O.

S203 in FIG. 23 (Calculation of Use Region and Use Frequency)

The spectacle lens design computer 202 calculates a use region (a region through which a visual line passes) on the spectacle lens model L and the use frequency in the region by the scheduled wearer S based on the visual line information. Specifically, the spectacle lens design computer 202 calculates an intersection between the unit vector (the direction of the visual line) of each visual line information having the origin at the eyeball rotation center Eo and the spectacle lens model L (e.g., the convex surface), and determines the use region from the distribution of the calculated intersections. Based on the unit vector and the time axis information of each visual line information, the spectacle lens design computer 202 calculates a time for which each visual line stays at each point in the use region, and determines the use frequency in the region from the calculated staying time at each point.

S204 in FIG. 23 (Setting of Principal Meridian)

The spectacle lens design computer 202 calculates a position (a point) at which the use frequency becomes high on the spectacle lens model L based on the use region and the use frequency calculated in step S203 (calculation of use region and use frequency) in FIG. 23, and draws a principal meridian on the spectacle lens model L by smoothly connecting neighboring calculated points with, for example, spline interpolation. The spectacle lens design computer 202 sets addition power distribution on the principal meridian based on the vector length (the distance information of the visual line) of each visual line information passing through the principal meridian drawn on the spectacle lens model. The addition power distribution is obtained, for example, by arranging a plurality of control points on the principal meridian, calculating the refractive power at each control point based on the vector length of the visual line information passing through each control point, and interpolating the refractive powers of the neighboring control points with, for example, spline interpolation, such as B-spline.

S205 in FIG. 23 (Control for Prismatic Effect in Horizontal Direction)

The spectacle lens design computer 202 defines a plurality of cross sectional curves extending in the horizontal direction from the principal meridian set in step S204 (setting of principal meridian) in FIG. 23, and sets refractive power distribution on each cross sectional curve according to the dioptric power distribution of each of a distance portion, a progressive power zone and a near portion.

S206 in FIG. 23 (Tentative Determination of Lens Surface Shape)

The spectacle lens design computer 202 tentatively determines a geometrical shape of a lens surface of the spectacle lens model L by smoothly connecting the refractive power distribution on the principal meridian and on each cross sectional curve extending in the horizontal direction, for example, using spline interpolation, and by converting the connected refractive power distribution into curvature distribution by a known conversion equation.

S207 in FIG. 23 (Ray Tracing Calculation)

The spectacle lens design computer 202 executes optimization calculation by ray tracing with respect to the tentatively determined spectacle lens model L, and thereby evaluates the use region calculated in step S203 (calculation of use region and use frequency) in FIG. 23. An evaluation value and an evaluation function defining a predetermined convergence condition for optimizing the use region may be arbitrarily set.

S208 in FIG. 23 (Judgment on Satisfaction of Convergence Condition)

The spectacle lens design computer 202 judges whether or not the predetermined convergence condition is satisfied based on evaluation results in step S207 (ray tracing calculation) in FIG. 23. When the spectacle lens design computer 202 judges that the predetermined convergence condition is not satisfied (S208 in FIG. 23: NO), the process proceeds to step S209 (fine adjustment of addition power distribution) in FIG. 23.

S209 in FIG. 23 (Fine Adjustment of Addition Power Distribution)

The spectacle lens design computer 202 makes fine adjustment to the addition power distribution by modifying the position and the refractive power of each control point on the principal meridian of the spectacle lens model so that the predetermined convergence condition is satisfied.

S210 in FIG. 23 (Control for Prismatic Effect in Horizontal Direction)

After the fine adjustment of the addition power distribution in step S209 (fine adjustment of addition power distribution) in FIG. 23, as in the case of step S205 (control for prismatic effect in horizontal direction) in FIG. 23, the spectacle lens design computer 202 defines a plurality of cross sectional curves extending in the horizontal direction from the principal meridian, and sets refractive power distribution on each cross sectional curve according to the dioptric power distribution of each of a distance portion, a progressive power zone and a near portion. Then, the spectacle lens design computer 202 causes the process of the flowchart to return to step S206 (tentative determination of lens surface shape) in FIG. 23.

Let us consider, for example, a case where it is judged in step S208 (judgment on satisfaction of convergence condition) in FIG. 23 that the predetermined convergence condition is satisfied (S208 in FIG. 23: YES) as a result of correction of the lens surface shape by repeating steps from S206 (tentative determination of lens surface shape) in FIG. 23 to step S210 (control for prismatic effect in horizontal direction) in FIG. 23. In this case, the spectacle lens design computer 202 calculates an aspherical surface correction amount according to the wearing condition (e.g., the lens pantoscopic angle and the lens face form angle), and adds the calculated aspherical surface correction amount to the tentative lens surface shape after step S206 (tentative determination of lens surface shape) in FIG. 23. As a result, the lens surface shape is determined, and the shape design of the progressive power lens is completed.

According to the design process, a progressive power lens which has suitable aberration distribution for an actual use condition and is suitable for use of each visual line and the visual distance by the scheduled wearer S can be designed.

Hereafter, two design examples (design examples 1 to 2) designed when different convergence conditions are used are explained.

Design Example 1

Figure 25B:
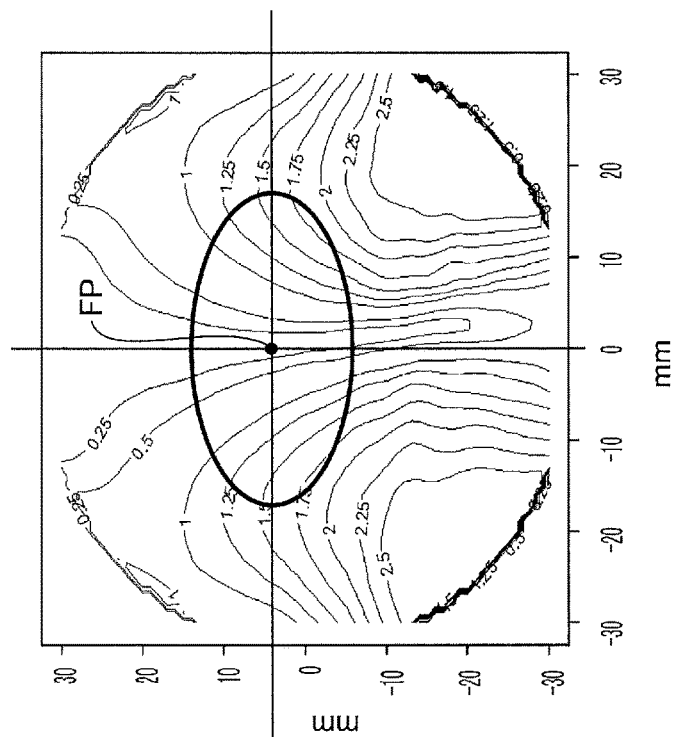
FIG. 25 illustrates astigmatism distribution before and after optimization according to a design example 1.
Figure 25A:
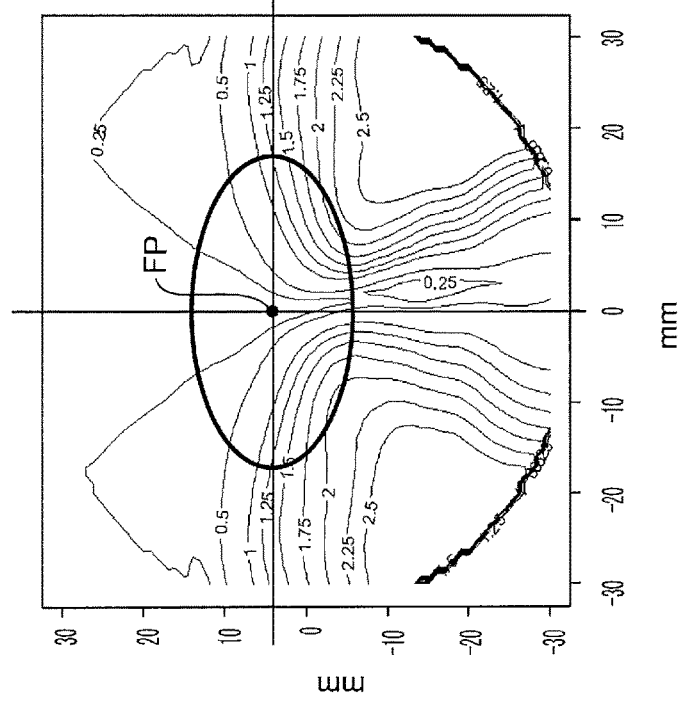

FIG. 25A shows transmission astigmatism distribution of a lens before optimization according to the design example 1, and FIG. 25B shows transmission astigmatism distribution of a lens after optimization according to the design example 1. In the design example 1, the evaluation function is defined such that the transmission astigmatism becomes lower than or equal to 2.0 diopter (2.0D) within the use region (a region surrounded by an ellipse in FIGS. 25A and 25B) calculated in step S203 (calculation of use region and use frequency) in FIG. 23. As shown in FIG. 25B, since the transmission astigmatism is suppressed to a value lower than or equal to 2.0D in the use region, shake and distortion in the use region are reduced.

Design Example 2

FIG. 26A shows distribution of logMAR visual acuity before optimization according to the design example 2, and FIG. 26B shows distribution of logMAR visual acuity after optimization according to the design example 2. Details about logMAR visual acuity can be seen, for example, in Japanese Patent Publication No. 4033344B. In the design example 2, the evaluation function is defined such that, within the use region in a distance portion situated on an upper side of the fitting point FP on the lens, an area in which the logMAR visual acuity becomes lower than or equal to 0.155 (0.7 or more in terms of decimal visual acuity) becomes larger than 190 $mm^2$ on the basis of an area on the distribution diagram (not on the basis of an area on the lens). As shown in FIG. 26B, in the design example 2, assuming a situation where a far point is mainly viewed, for example, during car driving, a wide range in which the scheduled wearer S can clearly recognize an object within the use region in the distance portion can be secured.

Five design examples (design examples 3-1 to 3-3 and design examples 4-1 to 4-2) of a progressive power lens using the visual line information according to the embodiment are explained. The design examples 3-1 to 3-3 relate to setting of an inside-shift amount of the principal meridian, and the design examples 4-1 to 4-2 relate to setting of an addition power curve.

Design Example 3-1

Figure 27B:
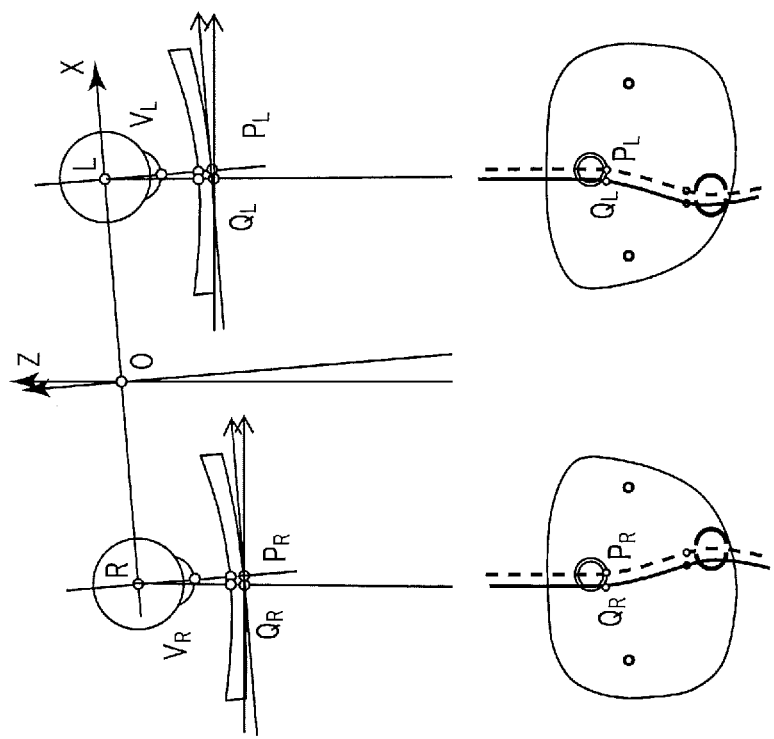
FIG. 27 is an explanatory illustration for explaining a state of a visual line in a design example 3-1.
Figure 27A:
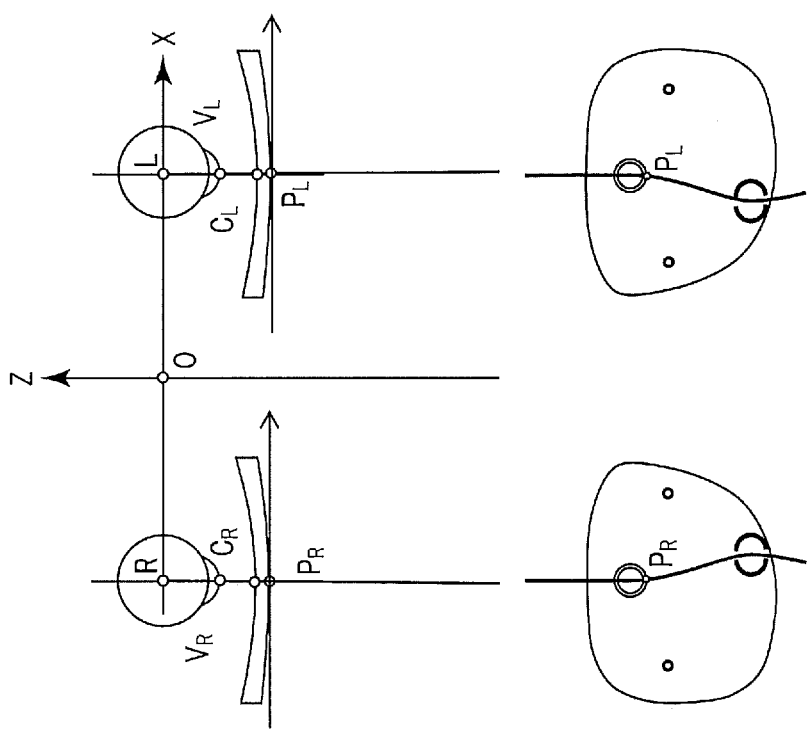

There is a case where a face of a person (the scheduled wearer S) is inclined even when the person thinks that he or she faces frontward. In such a case, even when a lens does not have a face form angle, the lens is apparently inclined with respect to the frontward visual line. To compare these situations, FIG. 27A shows a case where the face is not inclined, and FIG. 27B shows a case where the face is inclined. In each of these drawings, a top cross sectional view in a lens-worn state is illustrated on the upper side together with the head coordinate system, and a passing point of the frontward visual line on the lens is illustrated on the lower side.

In the state where the face is not inclined (FIG. 27A), the frontward visual lines pass through set positions $P_R$ and $P_L$ of the assumed pupillary distance. On the other hand, in the state where the face is inclined (FIG. 27B) (it is assumed that the head is inclined about the Y-axis by 10 degrees as an example), the actual frontward visual lines do not pass through the set positions $P_R$ and $P_L$ of the assumed pupillary distance, but pass through positions $Q_R$ and $Q_L$ which are shifted from the set positions $P_R$ and $P_L$. That is, the state shown in FIG. 27B corresponds to a state where the frame face form angle of 10 degrees is apparently added to the frontward visual lines.

In this design example, the prism correction and the aberration correction according to the apparent face from angle is applied to the design.

Figure 28:
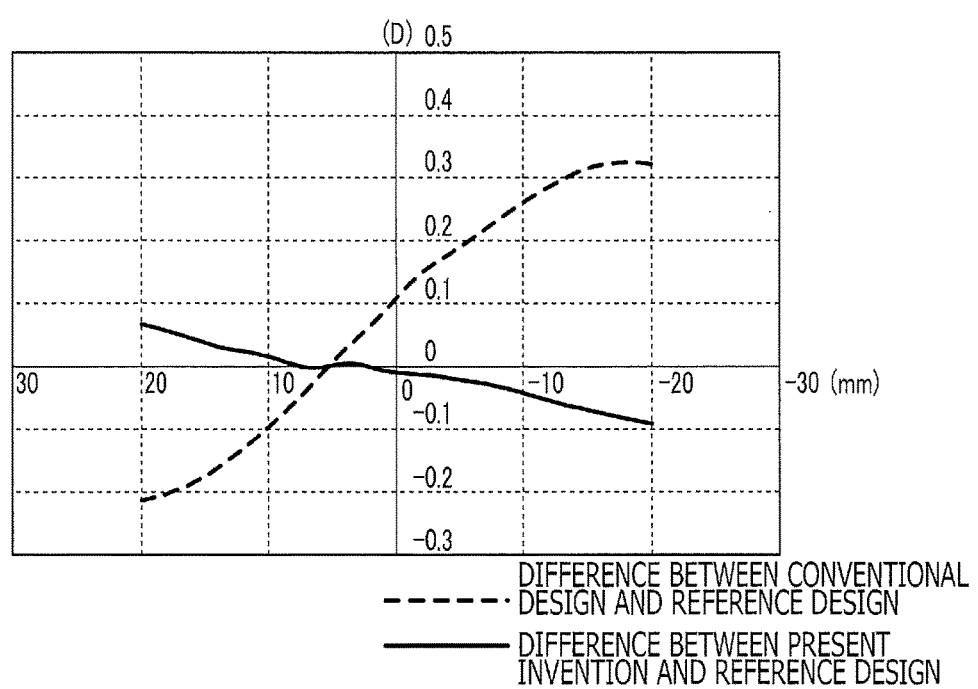
FIG. 28 is a graph illustrating average transmission dioptric power in the design example 3-1.

FIG. 28 is a diagram for explaining the comparison between a conventional design example (correction for the apparent face form angle is not executed) and the above described design example (correction (prism correction and aberration correction) according to the apparent face form angle). In this case, the calculation is made using S+3.00, ADD2.50D. Specifically, in FIG. 28, for each of the conventional design and the subject design example, the difference in average transmission dioptric power (on the basis of a convex surface coordinate of the right lens, the difference along the cross section at Y=0 mm, ±20 mm range along X-axis) with respect to reference design is graphically shown. In FIG. 28, a curve indicated by a dashed line represents the difference in average transmission dioptric power between the conventional design and the reference design, and a curve indicated by a solid line represents the difference in average transmission dioprtic power between the subject design example and the reference design.

As shown in FIG. 28, in the conventional design, the difference with respect to the reference design becomes larger than or equal to 0.3D. By contrast, according to the subject design example, the difference with respect to the reference design is suppressed to a value smaller than or equal to 0.1D.

Design Example 3-2

Figure 29:
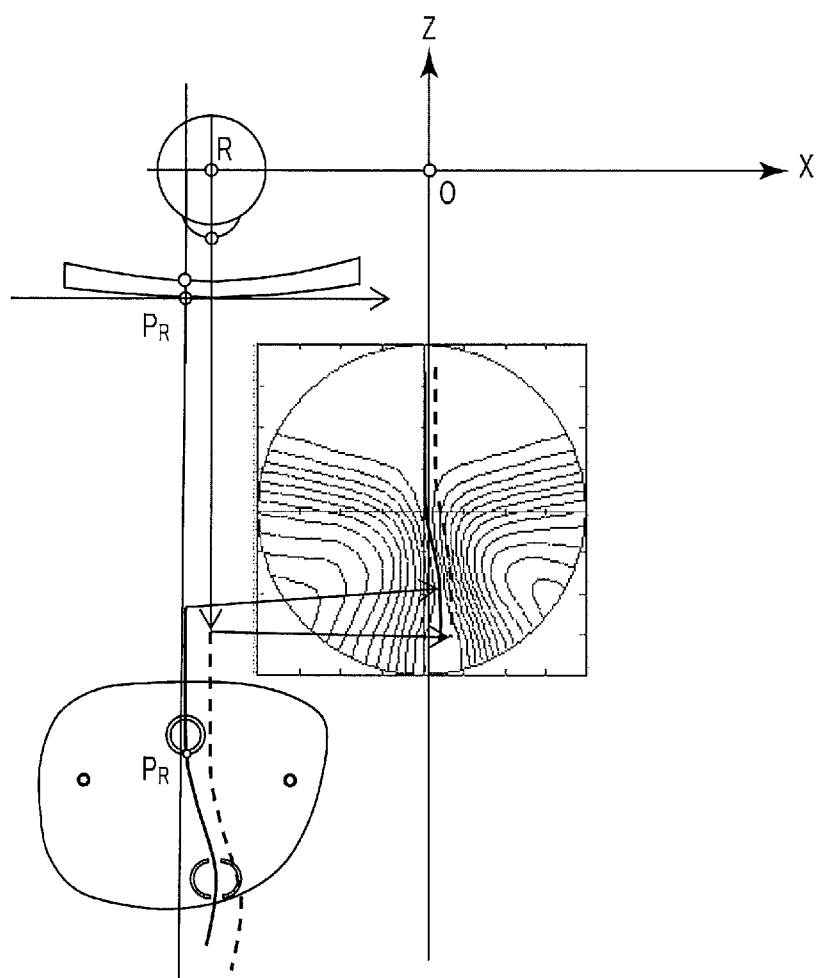
FIG. 29 is an explanatory illustration for explaining a state of pupillary distance PD in a design example 3-2.

There is a case where the difference is caused between actual visual line passing points and the pupillary distance PD assumed for the lens due to a measurement error of the pupillary distance PD. The subject design is an example for dealing with the above described case. FIG. 29 is an explanatory illustration for explaining the subject design under the situation. Here, we assume that the actual visual line shifts by 1 mm to the nose side with respect to the pupillary distance PD measured for the right eye. In such a situation, in the conventional design, since the lens deviates from the position of the frontward visual line, the measured pupillary distance PD also shifts and thereby the visual line for viewing a range of an intermediate point to a near point passes a position in a region where the astigmatism exists (see a visual line passing position indicated by a dashed line on the astigmatism diagram shown in FIG. 29).

On the other hand, as described above, since, according to the embodiment, the staying time information concerning the passing position of the visual line on the lens can be obtained, the pupillary distance PD can be altered according to the staying time information. Therefore, it becomes possible to cause the visual line for viewing a range of an intermediate point to a near point to pass through a position where the astigmatism is small.

Figure 30:
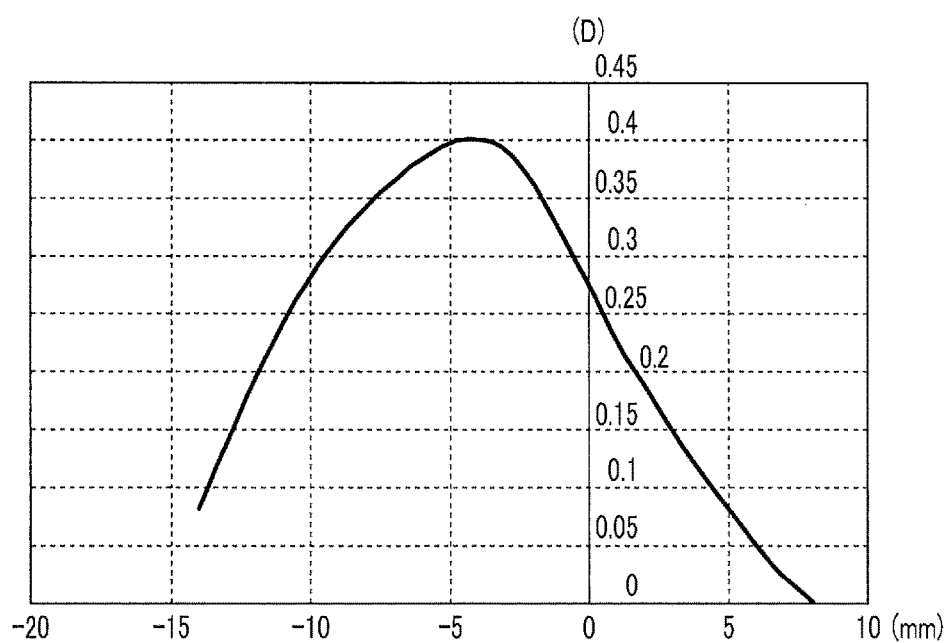
FIG. 30 is a graph illustrating a difference in transmission astigmatism between conventional design and the design example 3-2.

FIG. 30 illustrates the difference between the conventional design and the subject design in the above described situation. In this case, the calculation is made using S+0.00D, ADD2.50D. Specifically, FIG. 30 is a graph of the transmission astigmatism (on the basis of the convex surface coordinate) illustrating the comparison between the conventional design and the subject design. As shown in FIG. 30, in the case of the conventional design, the curve indicated by the dashed line in FIG. 29 becomes the principal meridian, and there is a difference at the maximum of 0.4D between the conventional design and the subject design where the pupillary distance PD is modified.

Design Example 3-3

Figure 31A:
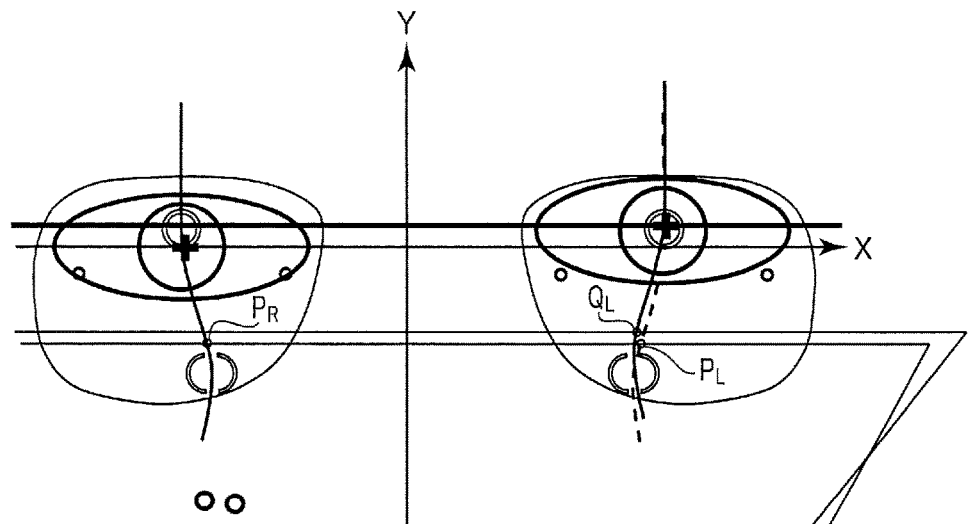
FIG. 31 is an explanatory illustration for explaining a position of an eye point, a visual line passing position and a state of addition power in a design example 3-3.

In the case where the eye points EP differ between the left and the right and thereby fitting points FP differ, if the downward rotation amount is the same for the left and the right, there is a possibility that the height and the inside-shift amount of the visual line passing position defined when a near point is viewed differ between the left and the right. Therefore, the height and the inside-shift amount need to be modified. FIG. 31A is an explanatory illustration for explaining such a situation. In this case, an example where the left FP is higher by 2 mm than the right FP is illustrated. As shown in FIG. 31A, regarding the left eye, the actual visual line passing position for the near vision shifts from PL to QL, and the inside-shift amount of the visual line also differs (in FIG. 31A, the actual visual line position is indicated by a curve of a solid line).

Figure 31B:
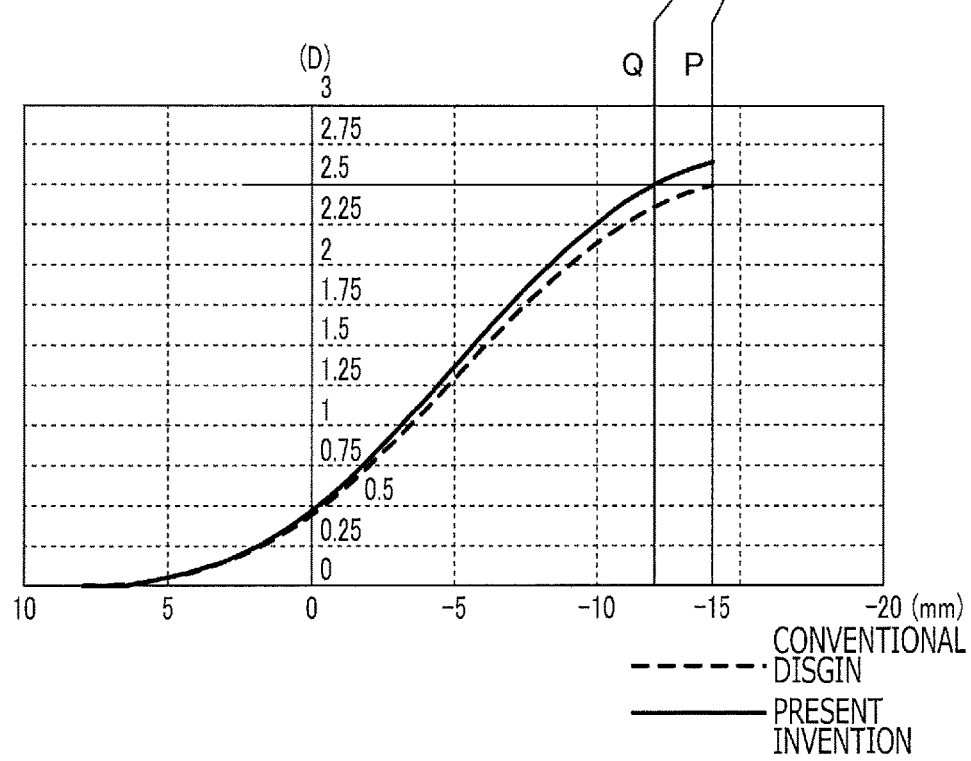

FIG. 31B is a graph illustrating an addition power curve, in which a curve indicated by a dashed line represents the addition power in the case of the conventional design, and a curve indicated by a solid line represents the addition power in the case of the subject design example. As shown in FIG. 31B, in the case of the conventional design, the addition power of 2.50D is obtained at the position $P_R$ of the right eye; however, only 2.36D is obtained at the position $Q_L$ of the left eye.

By contrast, according to the subject design example, the addition power of 2.50D can be secured at the position $Q_L$ by adjusting the addition power on the principal meridian from the visual line information.

Design Example 4-1

In the subject design example, an addition power curve is set from the near distance and the distance information on the fitting point FP according to the embodiment. For example, it is assumed that the ordered prescription is S0.00, ADD2.50D (40 cm in terms of the distance). Since, by the measurement, the distance information at the fitting pint FP is 1.7 m (corresponding to approximately 0.6D) and the near distance is 45 cm, the addition power of approximately 2.22D is sufficient and therefore the design is made in the condition of ADD2.22. That is, according to the subject design, S0.00D and ADD2.22D are used.

Figure 32:
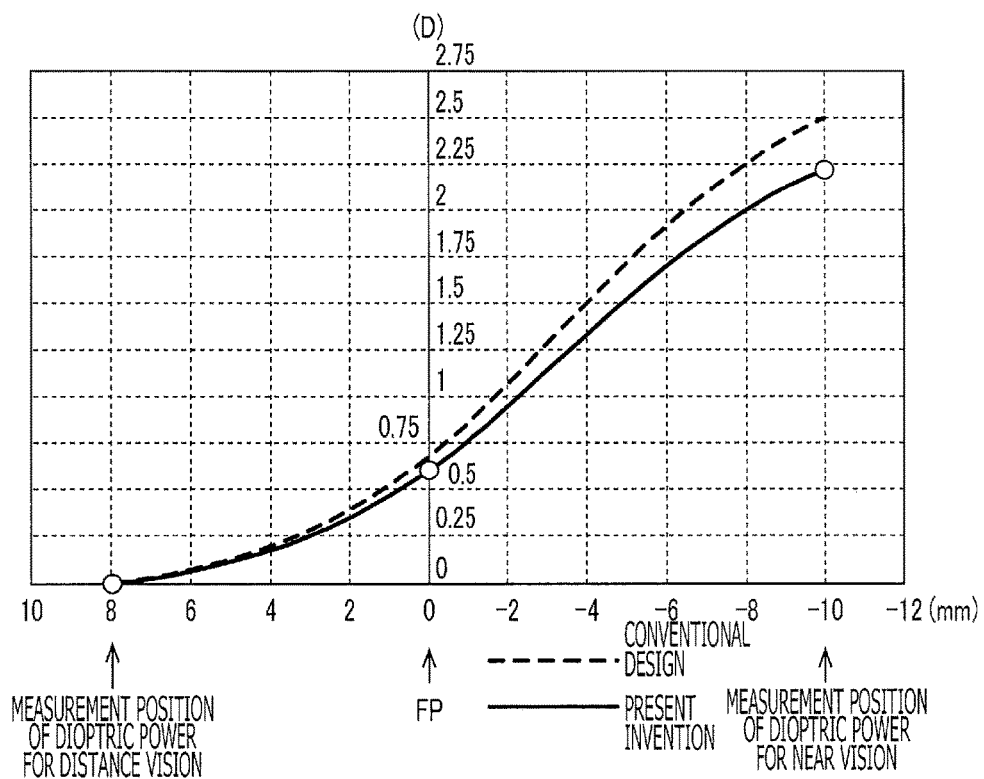
FIG. 32 is a graph illustrating an addition power curve according to a design example 4-1 and an addition power curve according to conventional design.

FIG. 32 is a graph illustrating an addition power curve according to the subject design example (a curve indicated by a solid line in FIG. 32), In FIG. 32, a graph illustrating an addition power curve according to the conventional design is also shown for comparison (a curve indicated by a dashed line in FIG. 32). As can be seen from FIG. 32, regarding the near distance, setting is made at a nearer distance than an actually used distance in the conventional design. Therefore, according to the conventional design, a wearer is conversely required to approach an object for near vision. Furthermore, in the conventional design, change in the addition power is large, and therefore the astigmatism becomes also large. As a result, an intermediate portion becomes narrow.

Figures 33A, 33B:
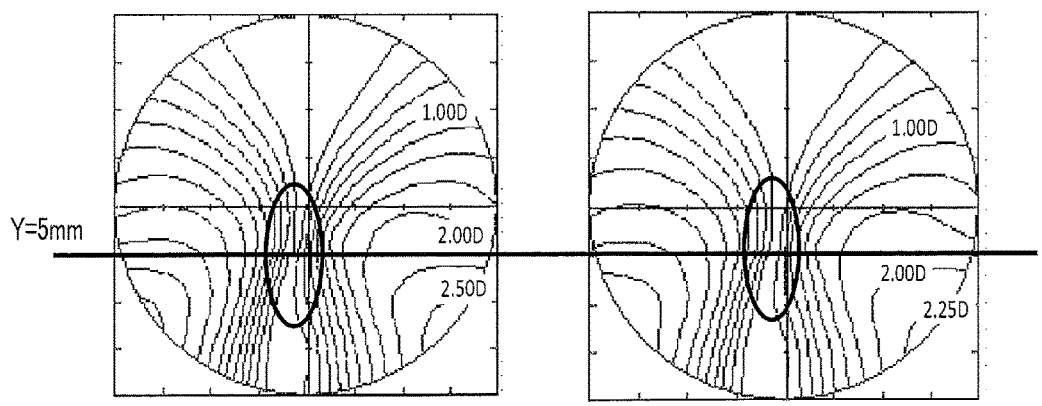
FIG. 33 illustrates transmission astigmatism in the design example 4-1 and transmission astigmatism in conventional design.

FIG. 33A illustrates transmission astigmatism according to the conventional design, and FIG. 33B illustrates transmission astigmatism according to the subject design. FIGS. 33A and 33B are based on a convex surface coordinate of a right lens, the range of Y-axis of ±20 mm, and the pitch of 5 mm As can be seen from FIG. 33, according to the conventional design, unnecessarily large addition power is added, and thereby the astigmatism becomes large. On the other hand, according to the subject design example, the addition power curve on the principal meridian can be designed such that a sufficient amount of addition power can be provided at the visual line passing position for near vision, and therefore the astigmatism can be reduced. Furthermore, according to the subject design example, the minimum value of the aberration is decreased and encroaching of the aberration is also suppressed, and as a result a wide intermediate portion can be secured. It should be noted that the transmission astigmatism diagram represents the astigmatism on a reference sphere having a radius defined from the eyeball rotation center to the vertex of the rear surface of the lens, and a light ray proceeds from an object and passes through the lens and the eyeball rotation center.

Figure 34:
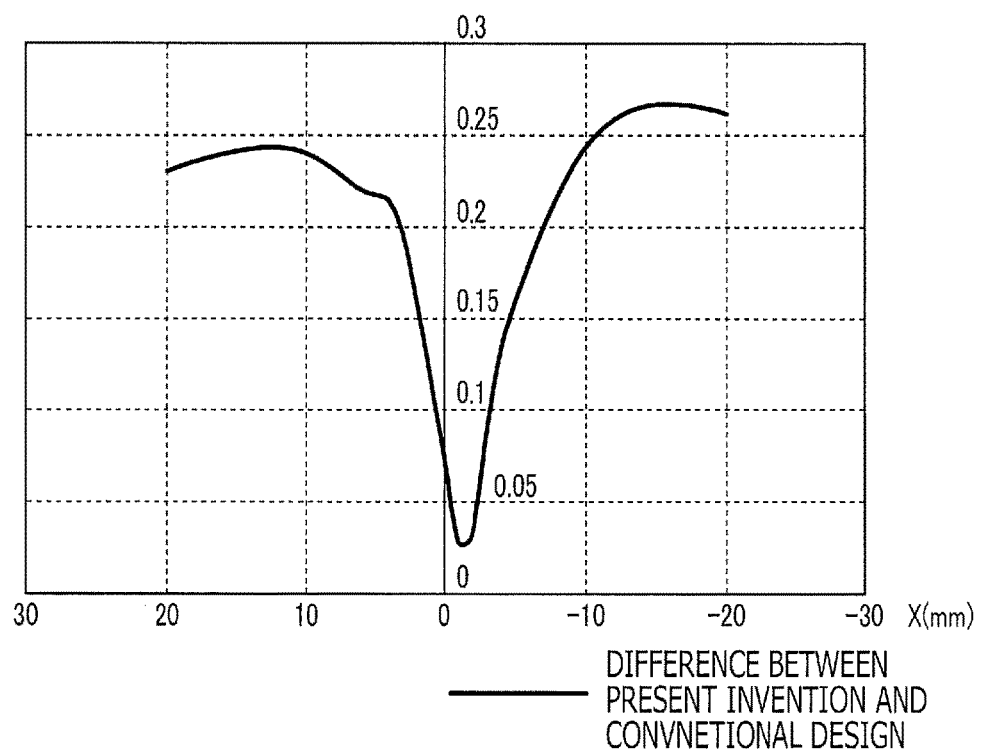
FIG. 34 is a graph illustrating a difference in transmission astigmatism between the design example 4-1 and conventional design.

FIG. 34 is a graph illustrating the difference in transmission astigmatism (on the basis of the convex surface coordinate of the right lens) between the subject design example and the conventional design. Specifically, the graph represents the difference in astigmatism in a cross sectional direction at Y=−5 mm, X=±20 mm. As can be seen from FIG. 34, the difference in astigmatism between the subject design example and the conventional design at Y=−5 mm, X=±20 mm is larger than or equal to 0.25D at most, and therefore it is understood that the subject design example is advantageous.

Design Example 4-2

The subject design example is an example where an addition power curve is set by considering the fitting point FP according to the embodiment and by further considering the distance information of a visual line for distance vision on the upper side of the fitting point FP. For example, it is assumed the ordered prescription is S0.00D, ADD2.50D. When the measured distance information of the visual line for distance vision is a finite distance (it is assumed that the distance is 2 m, for example), the design can be made by defining the dioptric power for distance vision as a value obtained by adding a dioptric power corresponding to the measured distance information to the ordered prescription. At a point for near vision, an addition power curve is set by converting the distance information into a dioptric power and by considering the dioptric power for distance vision obtained as above. For example, the design is made by (the dioptric power at a position for near vision)=(added infinite distance)+(change in addition power).

FIG. 35 is a graph illustrating an addition power curve according to the subject design example (a curve indicated by a solid line in FIG. 35). In FIG. 35, a graph illustrating an addition power curve according to the conventional design is also shown for comparison (a curve indicated by a dashed line in FIG. 35). As can be seen from FIG. 35, regarding distance vision, setting is made at a father distance than an actually used distance, accommodation is needed accordingly, and thereby the wearer may be fatigued. Furthermore, in the conventional design, change in the addition power is large, the astigmatism becomes larger, and thereby the size of the intermediate portion is reduced.

FIG. 36A illustrates the transmission astigmatism according to the conventional design (design by the ordered prescription is S0.00, ADD2.50D), and FIG. 36B illustrates the transmission astigmatism according to the subject design example (design in the condition of S0.50D, ADD2.00D). FIGS. 36A and 36B are based on a convex surface coordinate of a right lens, the range of Y-axis of ±20 mm, and the pitch of 5 mm. As can be seen from FIGS. 36A and 36B, according to the subject design example, since the dioptric power corresponding to the required distance (i.e., the measured distance) is added to the dioptric power for distance vision, a required dioptric power for near vision can be achieved at the visual line passing position for near vision even if the prescribed addition power is reduced. As a result, there is no necessity to add an extra addition power, and thereby it becomes possible to suppress the astigmatism. Furthermore, according to the subject design example, the maximum value of the aberration is decreased, encroaching of the aberration is also suppressed, and as a result a wide intermediate portion can be secured.

Figure 37:
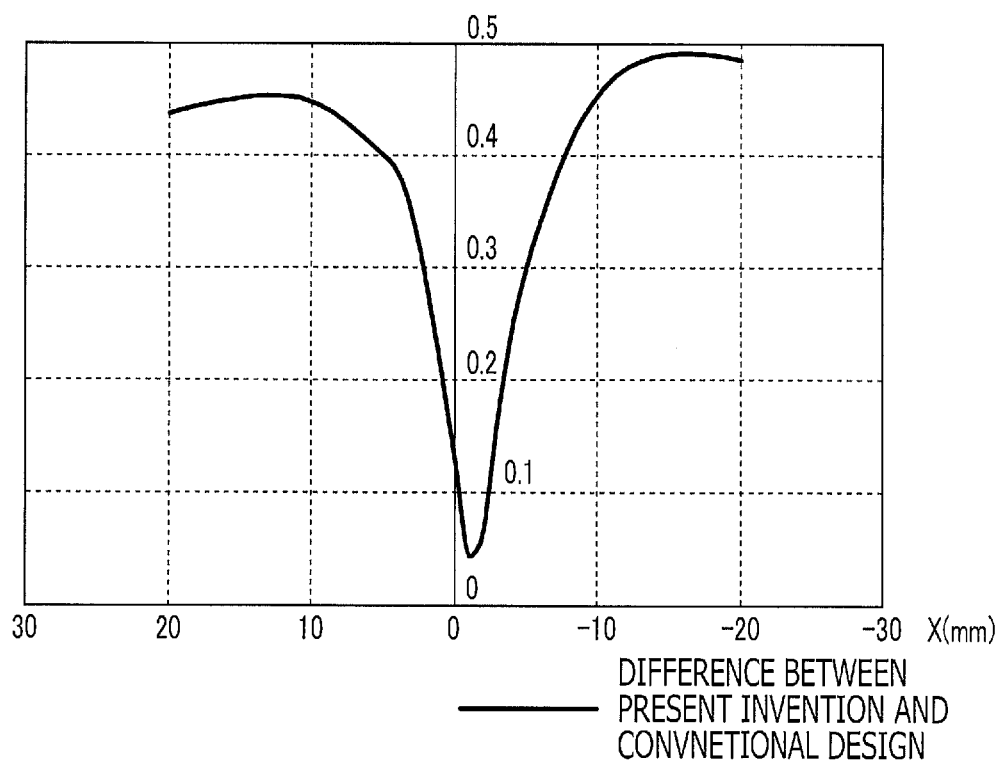
FIG. 37 is a graph illustrating a difference in transmission astigmatism between the design example 4-2 and conventional design.

FIG. 37 is a graph illustrating the difference in transmission astigmatism (on the basis of the convex surface coordinate of the right lens) between the subject design example and the conventional design. Specifically, the graph represents the difference in astigmatism in a cross sectional direction at Y=−5 mm, X=±20 mm. As can be seen from FIG. 37, the difference in astigmatism between the subject design example and the conventional design at Y=−5 mm, X=±20 mm is larger than or equal to 0.45D at most, and therefore it is understood that the subject design example is advantageous.

The transmission average dioptric power and the transmission astigmatism respectively represent an average dioptric power error and astigmatism caused on a sphere (the rear vertex sphere, V in FIG. 24) having a radius equal to a distance from the eyeball rotation center to the rear vertex of the lens defined for a right ray passing through the convex surface and the concave surface of the lens and further passing through the eyeball rotation center.

Design Example of Single-Vision Lens

Figure 38:
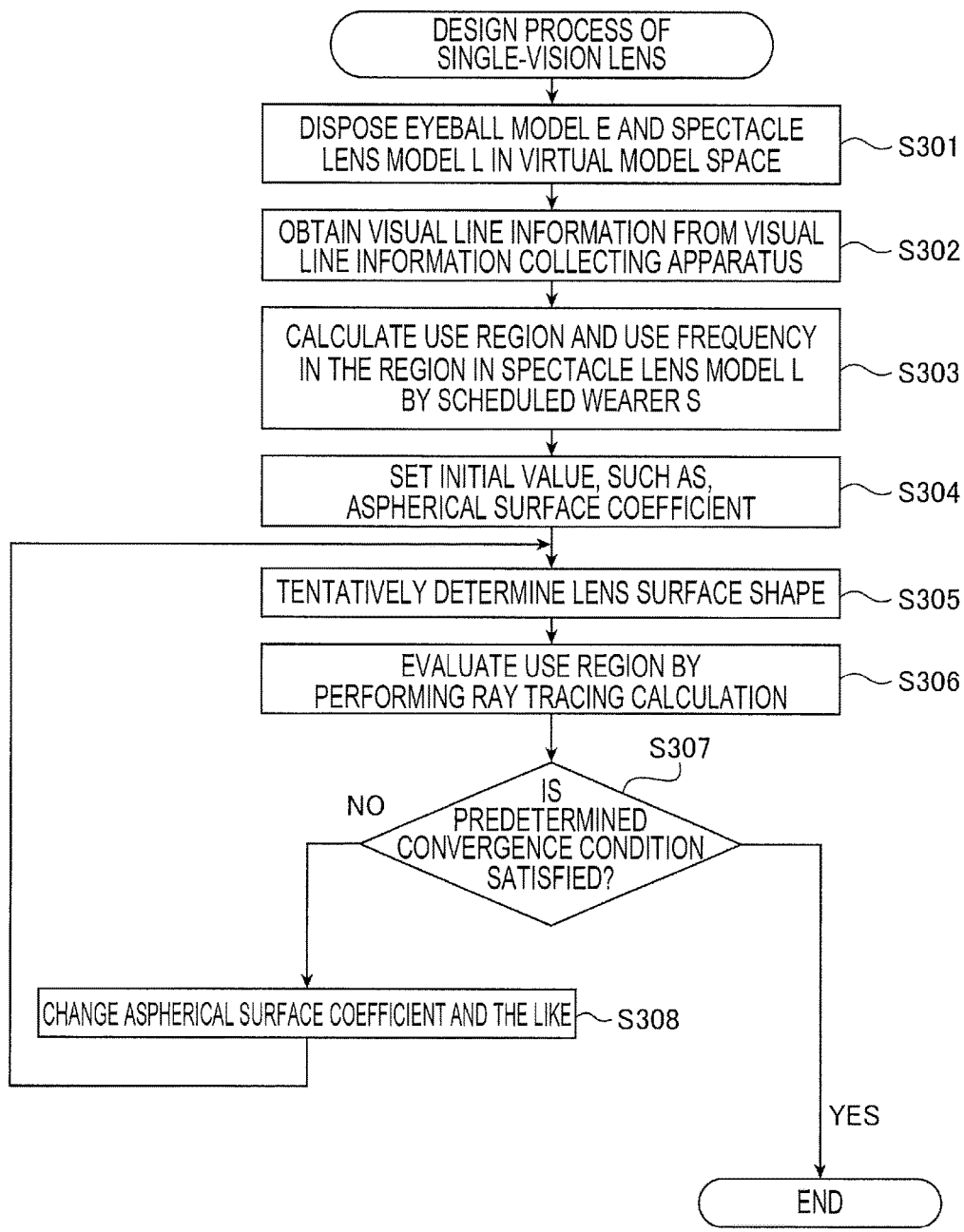
FIG. 38 is a flowchart illustrating a design process for a single-vision lens by the spectacle lens design computer.

FIG. 38 is a flowchart illustrating a design process for a single-vision lens by the spectacle lens design computer 202.

S301 (Construction of Virtual Model) to S303 (Calculation of Use Region and Use Frequency) in FIG. 38

The spectacle lens design computer 202 executes steps S301 (construction of virtual model), S302 (obtaining of visual line information) and S303 (calculation of use region and use frequency) in FIG. 38. An initial spectacle lens model L of the subject design example is, for example, a spherical lens having a spherical shape selected based on the prescription. Since these steps are similar to step S201 (construction of virtual model), S202 (obtaining of visual line information) and S203 (calculation of use region and use frequency) in FIG. 23, specific explanation thereof is omitted.

S304 in FIG. 38 (Initial Setting, such as, Aspherical Coefficient)

The spectacle lens design computer 202 sets initial values of parameters concerning the aspherical coefficient and a free-form surface based on the initial spectacle lens model L in accordance with the use region and the use frequency calculated in step S303 (calculation of use region and use frequency) in FIG. 38.

S305 in FIG. 38 (Tentative Determination of Lens Surface Shape)

The spectacle lens design computer 202 tentatively determines a geometrical shape of a lens surface of the spectacle lens model L based on the parameters concerning the aspherical surface coefficient and the free-from surface.

S306 in FIG. 38 (Ray Tracing Calculation)

The spectacle lens design computer 202 executes optimization calculation by ray tracing with respect to the tentatively determined spectacle lens model L, and thereby evaluates the use region calculated in step S303 (calculation of use region and use frequency) in FIG. 38.

S307 in FIG. 38 (Judgment on Satisfaction of Convergence Condition)

The spectacle lens design computer 202 judges whether or not the predetermined convergence condition is satisfied based on evaluation results in step S306 (ray tracing calculation) in FIG. 38. When the spectacle lens design computer 202 judges that the predetermined convergence condition is not satisfied (S307 in FIG. 38: NO), the process proceeds to step S308 (change of aspherical coefficient and etc.) in FIG. 38, S308 in FIG. 38 (Change of Aspherical Coefficient and Etc.)

The spectacle lens design computer 202 changes the parameters concerning the aspherical coefficient and the free-form surface so that the predetermined convergence condition is satisfied. Then, the spectacle lens design computer 202 controls the process of the flowchart to return to step S305 (tentative determination of lens surface shape) in FIG. 38.

For example, let us consider a case where it is judged that the predetermined convergence condition is satisfied (S307 in FIG. 38: YES) as a result of correction of the lens surface shape by repeating steps from S305 (tentative determination of lens surface shape) in FIG. 38 to S308 (change of aspherical coefficient and etc.) in FIG. 38. In this case, the spectacle lens design computer 202 calculates an aspherical surface correction amount according to the wearing condition (e.g., a lens pantoscopic angle, a lens face form angle), and adds the aspherical surface correction amount to the tentative lens surface shape after execution of step S305 (tentative determination of lens surface shape) in FIG. 38. As a result, the lens surface shape is determined, and the shape design of the single-vision lens is completed.

According to the subject design process, the single-vision lens which has suitable aberration distribution for an actual use condition and is suitable for use of each visual line and the visual distance by the scheduled wearer S can be designed.

In the foregoing, an example where a progressive power lens or a single-vision lens is designed using the visual line information of the scheduled wearer S; however, in another embodiment, a spectacle lens most suitable for the condition corresponding to the visual line information of the scheduled wearer S may be selected from a plurality of types of preset spectacle lenses.

The spectacle lens design computer 202 may display, on the monitor 152d through the host computer 200 and via the Internet, information concerning the transmission astigmatism distribution, the transmission average dioptric power distribution, the logMAR visual acuity distribution of the designed lens, a performance index described in patent document 2 (Japanese Patent Publication No. 3919097B), an RGB image obtained by the photographing apparatus or another RGB image, a diagram in which image processing is executed for each pixel according to aberration of a light ray with respect to a three-dimensional virtual object image, and an image in which the frequency of the visual line passing points are superimposed on the above described information as contour lines, shading, dots, etc. Such representation may be performed by superimposing an image of a lens cut in a shape of a frame on the image of the above described distribution diagram, the RGB image or the three dimensional virtual image. Examples of such displayed images are illustrated in FIGS. 39A and 39B. Each of FIGS. 39A and 39B schematically illustrates an image in which a design result, a frame and the visual line information are arranged to overlap with each other, and represents the distribution of the logMAR as a result of design shown in FIG. 26. Specifically, FIG. 39A illustrates a case where the visual line staying time and the passing position are represented by contour lines, and FIG. 39B is a case where the visual line passing points are plotted.

The foregoing is the explanation about the embodiment of the invention. Embodiments according to the invention are not limited to the above described examples, and various types of variations can be made within the scope of the technical concept of the invention. For example, embodiments may include examples and variations described herein by way of illustration or modifications thereof combined in an appropriate manner.

What is claimed is:

1. A spectacle lens design system, comprising:
    an eyeball rotation center determination unit configured to identify a corneal apex position of an eye of a subject based on an image photographed by a predetermined photographing apparatus and determine an eyeball rotation center position of the subject based on the identified corneal apex position;
    a visual line information calculation unit configured to calculate visual line information of the subject defined when the subject watches a visual target disposed at a predetermined position, based on the eyeball rotation center position determined by the eyeball rotation center determination unit and the position of the visual target; and
    a shape design unit configured to design a shape of a spectacle lens based on predetermined prescription information and the visual line information calculated by the visual line information calculation unit.

2. The spectacle lens design system according to claim 1, further comprising a wearing parameter calculation unit configured to calculate a wearing parameter based on the corneal apex position of the eye identified based on the image photographed by the predetermined photographing apparatus, wherein the shape design unit designs the shape of the spectacle lens using the wearing parameter calculated by the wearing parameter calculation unit.

3. The spectacle lens design system according to claim 2, wherein the wearing parameter includes at least one of a frame pantoscopic angle, a frame face form angle, a frame vertex distance, a pupillary distance and a near working distance.

4. The spectacle lens design system according to claim 2, wherein the wearing parameter calculation unit continuously calculates wearing parameter values as time series data, and determines a true wearing parameter by using the wearing parameter values calculated continuously as the time series data.

5. The spectacle lens design system according to claim 1, wherein: when a coordinate system whose origin is equal to a reference point set at the predetermined photographing apparatus is defined as a photographing apparatus coordinate system, and a coordinate system whose origin is equal to a reference point set at a head of the subject is defined as a head coordinate system, the eyeball rotation center determination unit operates to:
calculate a position and a pose of the head of the subject in the photographing apparatus coordinate system based on the image photographed by the predetermined photographing apparatus;
define the head coordinate system based on the calculated position and the pose of the head of the subject;
convert a coordinate of the corneal apex position in the photographing apparatus coordinate system to the corneal apex position in the head coordinate system by making directions of coordinate axes of the defined head coordinate system and directions of coordinate axes of the defined photographing apparatus coordinate system coincide with each other by performing a predetermined coordinate conversion; and
obtain a coordinate of a position of the eyeball rotation center by adding a default value to the coordinate of the corneal apex position in the converted head coordinate system.

6. The spectacle lens design system according to claim 5, further comprising:
a detection unit configured to detect, at predetermined time intervals, the position and the pose of the head based on the image photographed by the predetermined photographing apparatus or detected data by a detecting apparatus capable of detecting the position and the pose of the head of the subject; and
a pseudo moving unit configured to move, at predetermined time intervals, the position of the visual target, in a pseudo manner, by an amount corresponding to a difference of the position of the head before and after detection by the detection unit and a difference of the pose of the head before and after detection by the detection unit so that the position and the pose of the head of the subject is maintained, in the pseudo manner, before and after the detection, wherein the visual line information calculation unit calculates the visual line information based on the determined eyeball rotation center position and the position of the visual target moved in the pseudo manner.

7. The spectacle lens design system according to claim 1, wherein:
the image is photographed by the predetermined photographing apparatus at a predetermined frame rate; and
in the eyeball rotation center determination unit, tentative positions of the eyeball rotation center are calculated for a predetermined number of frame images by determining eyeball rotation center positions for a predetermined number of frames, and a true eyeball rotation center position is determined based on the calculated tentative positions in the predetermined number of frame images.

8. The spectacle lens design system according to claim 1, wherein the visual line information is vector information of a visual line including a vector length and a unit vector of a visual line connecting the eyeball rotation center position with the position of the visual target.

9. The spectacle lens design system according to claim 8, wherein the visual line information further includes time axis information of a visual line.

10. The spectacle lens design system according to claim 9, further comprising:
a tentative shape design unit configured to design a tentative shape of the spectacle lens based on predetermined prescription information;
a use calculation unit configured to calculate a position on a spectacle lens through which a visual line defined when the subject wears a spectacle lens having the tentative shape passes, and a staying time of the visual line at the calculated position on the spectacle lens, based on the vector length, the unit vector and the time axis information of the visual line included in the visual line information calculated by the visual line information calculation unit, and thereby to calculate a use region and a use frequency in the spectacle lens by the subject; and
a correction unit that corrects the tentative shape based on the calculated use region and the use frequency.

11. The spectacle lens design system according to claim 1, further comprising a visual line information displaying unit configured to display, information concerning the calculated visual line information.

12. A spectacle lens supply system, comprising:
a spectacle lens design system according to claim 1; and
a spectacle lens manufacturing apparatus configured to manufacture spectacle lenses using the designed shape of the spectacle lens created by the spectacle lens design system.

13. A spectacle lens design method, comprising:
photographing a subject with a predetermined photographing apparatus;
identifying corneal apex position of an eye of the subject based on an image photographed with the predetermined photographing apparatus;
determining an eyeball rotation center position of the subject based on the identified corneal apex position;
calculating visual line information of the subject defined when the subject watches a visual target disposed at a predetermined position, based on the eyeball rotation center position and the position of the visual target; and
designing a shape of a spectacle lens based on predetermined prescription information and the visual line information.

14. The spectacle lens design method according to claim 13, further comprising: calculating a wearing parameter based on the corneal apex position of the eye identified based on the image photographed by the predetermined photographing apparatus, wherein the shape of the spectacle lens is designed using the calculated wearing parameter.

15. The spectacle lens design method according to claim 14, wherein the wearing parameter includes at least one of a frame pantoscopic angle, a frame face form angle, a frame vertex distance, a pupillary distance and a near working distance.

16. The spectacle lens design system according to claim 14, wherein wearing parameter values are continuously calculated as time series data, and a true wearing parameter is determined by using the wearing parameter values calculated continuously as the time series data.

17. A spectacle lens manufacturing method, comprising:
a spectacle lens manufacturing process of manufacturing the spectacle lens based on the shape of the spectacle lens designed by the design method according to claim 13.

* * * * *